US009138467B2

(12) United States Patent
Szathmary et al.

(10) Patent No.: US 9,138,467 B2
(45) Date of Patent: Sep. 22, 2015

(54) IMMUNOLOGICALLY ACTIVE COMPOSITIONS

(75) Inventors: Susan Szathmary, Carlsbad, CA (US); Laszlo Stipkovits, Rancho Santa Fe, CA (US); Peter Grandics, Carlsbad, CA (US)

(73) Assignee: STIPKOVITS, LASZLO, DR., Carlsbad ( * ) Notice: Subject to any disclaimer, the term of this patent is extended or adjusted under 35 U.S.C. 154(b) by 1560 days.

(21) Appl. No.: 11/814,355

(22) PCT Filed: Jan. 30, 2006

(86) PCT No.: PCT/US2006/003349
§ 371 (c)(1),
(2), (4) Date: Aug. 11, 2008

(87) PCT Pub. No.: WO2006/081576
PCT Pub. Date: Aug. 3, 2006

(65) Prior Publication Data
US 2011/0117204 A1    May 19, 2011

Related U.S. Application Data

(60) Provisional application No. 60/648,165, filed on Jan. 28, 2005.

(51) Int. Cl.
| A61K 39/00 | (2006.01) |
| A61K 39/02 | (2006.01) |
| A61K 39/385 | (2006.01) |
| C07K 14/30 | (2006.01) |

(52) U.S. Cl.
CPC ........... *A61K 39/0241* (2013.01); *A61K 39/385* (2013.01); *C07K 14/30* (2013.01); *A61K 2039/552* (2013.01); *A61K 2039/55516* (2013.01); *A61K 2039/55561* (2013.01); *A61K 2039/55572* (2013.01); *A61K 2039/55583* (2013.01); *A61K 2039/57* (2013.01); *A61K 2039/6087* (2013.01)

(58) Field of Classification Search
None
See application file for complete search history.

(56) References Cited

U.S. PATENT DOCUMENTS

| 5,603,960 | A | 2/1997 | O'Hagan et al. |
| 5,801,063 | A | 9/1998 | Grandics et al. |
| 6,521,431 | B1 | 2/2003 | Kiser et al. |
| 7,427,629 | B2 | 9/2008 | Kedl et al. |
| 2002/0061312 | A1 | 5/2002 | Medzhitov |
| 2003/0023993 | A1 | 1/2003 | Medzhitov et al. |
| 2003/0157539 | A1 | 8/2003 | Flavell et al. |
| 2003/0161797 | A1 | 8/2003 | Miller et al. |
| 2003/0175287 | A1 | 9/2003 | Medzhitov et al. |
| 2003/0224388 | A1 | 12/2003 | Flavell et al. |
| 2003/0232055 | A1 | 12/2003 | Medzhitov |
| 2004/0091491 | A1 | 5/2004 | Kedl et al. |
| 2004/0141950 | A1 | 7/2004 | Noelle et al. |
| 2004/0180919 | A1 | 9/2004 | Miller et al. |
| 2004/0181130 | A1 | 9/2004 | Miller et al. |
| 2004/0202720 | A1 | 10/2004 | Wightman et al. |
| 2004/0258698 | A1 | 12/2004 | Wightman et al. |
| 2004/0265351 | A1 | 12/2004 | Miller et al. |
| 2005/0048072 | A1 | 3/2005 | Kedl et al. |
| 2005/0054665 | A1 | 3/2005 | Miller et al. |
| 2005/0096259 | A1 | 5/2005 | Tomai et al. |
| 2005/0158325 | A1 | 7/2005 | Hammerbeck et al. |
| 2005/0163764 | A1 | 7/2005 | Medzhitov et al. |
| 2005/0165043 | A1 | 7/2005 | Miller et al. |
| 2005/0239735 | A1 | 10/2005 | Miller et al. |
| 2006/0045885 | A1 | 3/2006 | Kedl et al. |
| 2006/0045886 | A1 | 3/2006 | Kedl |
| 2006/0051374 | A1 | 3/2006 | Miller et al. |
| 2006/0121460 | A1 | 6/2006 | Medzhitov |
| 2006/0130164 | A1 | 6/2006 | Medzhitov et al. |
| 2006/0142202 | A1 | 6/2006 | Alkan et al. |
| 2006/0142235 | A1 | 6/2006 | Miller et al. |
| 2006/0188933 | A1 | 8/2006 | Flavell et al. |
| 2006/0189644 | A1 | 8/2006 | Wightman |
| 2006/0195067 | A1 | 8/2006 | Wolter et al. |
| 2006/0292168 | A1 | 12/2006 | Pethe et al. |
| 2007/0087009 | A1 | 4/2007 | Burdin et al. |
| 2007/0122421 | A1 | 5/2007 | Medzhitov |
| 2007/0160623 | A1 | 7/2007 | Medzhitov et al. |
| 2008/0096250 | A1 | 4/2008 | Medzhitov et al. |
| 2008/0193468 | A1 | 8/2008 | Levy et al. |
| 2008/0226667 | A1 | 9/2008 | Medzhitov |
| 2009/0081725 | A1 | 3/2009 | Powell et al. |

FOREIGN PATENT DOCUMENTS

| EP | 0941736 A1 | 9/1999 |
| JP | 11255664 A | 9/1998 |
| WO | WO/03/028661 A2 | 4/2003 |
| WO | WO/03/051351 A1 | 6/2003 |
| WO | WO2005060966 A1 | 7/2005 |
| WO | 2007/013893 A1 | 2/2007 |
| WO | 2007/052058 A1 | 5/2007 |
| WO | 2007/100699 A1 | 9/2007 |
| WO | 2008/051245 A1 | 5/2008 |

OTHER PUBLICATIONS

Strindelius et al. (Infect. Immun., 70:1434-1442, 2002).*
D.T. O'Hagan et al., "Microparticles for the Delivery of DNA Vaccines," Immunol. Rev. 199: 191-200 (2004).
T.B.H. Geijtenbeek et al., "Mycobacteria Target DC-SIGN to Suppress Dendritic Cell Function," J. Exp. Med. 197: 7-17 (2002).

(Continued)

*Primary Examiner* — Brian J Gangle
(74) *Attorney, Agent, or Firm* — Ditthavong & Steiner, P.C.

(57) ABSTRACT

This invention provides a microparticle carrier system comprising of one or more proteins, peptides, nucleic acids, carbohydrates, lipids or other bioactive substances with or without targeting molecules attached. In addition, the invention also provides immune modulatory compositions and methods of eliciting protective immune responses both in uninfected and infected hosts as well as the induction of immune tolerance.

28 Claims, 5 Drawing Sheets

(56) References Cited

OTHER PUBLICATIONS

C. Hu et al., "Mycobacterium tuberculosis Infection in Complement Deficient Mice," J. Immunol. 165: 2596-2602 (2000).
C. Reis E Sosa, "Activation of Dendritic Cells: Translating Innate into Adaptive Immunity," Curr. Opin. Immunol. 16: 21-25 (2004).
T. Beyer et al., "Bacterial Carriers and Virus-Like-Particles as Antigen Delivery Devices: Role of Dendritic Cells in Antigen Presentation," Curr. Drug Targets-Infect. Disord. 1:287-302 (2001).
K. Shortman et al., "Mouse and Human Dendritic Cell Subtypes," Nat. Rev. Immunol. 2: 151-61 (2002).
D. Brayden, "Oral Vaccination in Man Using Antigens in Particles: Current Status," Eur. J. Pharm. Sci. 14:183-189 (2001).
S. Szathmary et al., "Binding of Mycoplasmas to Solid Phase Adsorbents," Acta. Vet. Hung. 53:299-307 (2005).
T. Wadström & Å. Ljungh, "Glycosaminoglycan-Binding Microbial Proteins in Tissue Adhesion and Invasion: Key Events in Microbial Pathogenicity," J. Med. Microbiol. 48:223-233 (1999).
E.J. McKay, "A Simple Two-Step Procedure for the Purification of Plasma C1q from Different Animal Species," Immunol. Lett. 3:303-308 (1981).
G. Napolitani et al., "Selected Toll-Like Receptor Agonist Combinations Synergistically Trigger a T Helper Type 1-Polarizing Program in Dendritic Cells," Nature Immunol. 6: 769-776 (2005).
M. Singh et al., "Cationic Microparticles Are an Effective Delivery System for Immune Stimulatory CpG DNA," Pharm. Res. 18: 1476-1479 (2001).
D.C. Jackson et al., "A Totally Synthetic Vaccine of Generic Structure that Targets Toll-Like Receptor 2 on Dendritic Cells and Promotes Antibody or Cytotoxic T Cell Responses," Proc. Natl. Acad. Sci. USA 101: 15440-15445 (2004).
E.A. Koppel et al., "Identification of the Mycobacterial Carbohydrate Structure that Binds the C-Type Lectins DC-SIGN, L-SIGN, and SIGNR1," Immunobiology 209: 117-127 (2004).
N. Maeda et al., "The Cell Surface Receptor DC-SIGN Discriminates Between Mycobacterium Species Through Selective Recognition of the Mannose Caps on Lipoarabinomannan," J. Biol. Chem. 278: 5513-5516 (2003).
M. Parra et al., "The Mycobacterial Heparin-Binding Hemagglutinin Is a Protective Antigen in the Mouse Aerosol Challenge Model of Tuberculosis," Infect. Immun. 6799-6805 (2004).
S. Szathmary, "Immunomodulation of Pathogen-Host Interactions" (Doctoral Thesis, Szent István University, Budapest, Hungary, 2005).
Diwan, M. et al., "Biodegradable Nanoparticle Mediated Antigen Delivery to Human Cord Blood Derived Dendritic Cells for Induction of Primary T Cell Responses," J. Drug Targeting 11: 495-507 (2003).
Franz, J., et al., "Adjuvant Efficacy of Gelatin Particles and Microparticles," Internat. J. Pharmaceutics 168: 153-161 (1998).
Strindelius, L., et al., "Mucosal Immunization with Purified Flagellin from Salmonella Induces Systemic and Mucosal Immune Responses in C3H/HeJ Mice," Vaccine 22: 3797-3808.
A. Esauisabel et al., "Preparation and Stability of Agarose Microcapsules Containing BCG", J. Microencapsulation 19: 237-244 (2002), pp. 237-244.
E. Johnston & T. Eskeland, "Complement (C3)-Receptor-Mediated Phagocytosis of Agarose Beads by Mouse Macrophages II. Extracellular Activation of Macrophage-Derived Complemetn on Agarose via the Alternative Pathway," Scand. J. Immunol. 18: pp. 169-174 (1983).
E.S. Stanislavsky et al., R-Form Lipopolysaccharide (LPS) of Gram-Negative Bacteria as Possible Vaccine Antigens, FEMS Immunol. Med. Microbiol. 18: 139-143 (1997).

\* cited by examiner

```
                        SEQUENCE LISTING

<160> NUMBER OF SEQ ID NOS: 6

<210> SEQ ID NO 1
<211> LENGTH: 34
<212> TYPE: PRT
<213> ORGANISM: Mycoplasma gallisepticum

<400> SEQUENCE: 1

Lys Leu Ala Leu Thr Ser Glu Ile Thr Glu Glu Ile Tyr Pro Ser Ala
1               5                   10                  15

Pro Lys Val Ser Arg Lys Gln Arg Gly Val His Gly Phe Ser Glu Pro
            20                  25                  30

Thr Ser

<210> SEQ ID NO 2
<211> LENGTH: 17
<212> TYPE: PRT
<213> ORGANISM: Mycoplasma gallisepticum

<400> SEQUENCE: 2

Leu Leu Ala Lys Lys Thr Asp Lys Ser Val Ser Pro Gln Ala Ser Leu
1               5                   10                  15

Thr

<210> SEQ ID NO 3
<211> LENGTH: 7
<212> TYPE: PRT
<213> ORGANISM: Artificial Sequence
<220> FEATURE:
<223> OTHER INFORMATION: Synthesized linker sequence

<400> SEQUENCE: 3

Leu Ile Lys Phe Arg Ser Asn
1               5

<210> SEQ ID NO 4
<211> LENGTH: 10
<212> TYPE: PRT
<213> ORGANISM: Mycoplasma gallisepticum

<400> SEQUENCE: 4

Leu Leu Ala Lys Lys Thr Asp Lys Ser Val
1               5                   10
```

-continued

```
<210> SEQ ID NO 5
<211> LENGTH: 16
<212> TYPE: PRT
<213> ORGANISM: Mycoplasma gallisepticum

<400> SEQUENCE: 5

Leu Leu Ala Lys Lys Thr Asp Lys Ser Val Ser Pro Ala Gln Ala Ser
1               5                   10                  15

<210> SEQ ID NO 6
<211> LENGTH: 4
<212> TYPE: PRT
<213> ORGANISM: Mycoplasma gallisepticum

<400> SEQUENCE: 6

Arg Lys Gln Arg
1
```

IMMUNOLOGICALLY ACTIVE COMPOSITIONS

BACKGROUND OF THE INVENTION

This invention provides immunologically active compositions that can induce protective immunity or tolerance. The composition to induce protective immunity both in uninfected or infected host consists of antigenic epitopes but excludes or eliminates epitopes that participate in immune "escape" or induce tolerance. Protective immunity can be induced also by a composition that includes a pathogen associated molecular pattern(s) and/or a carrier with or without the antigenic epitopes. Another immunologically active composition that induces tolerance includes an escape epitope(s) or a molecular pattern(s) important for pathogen escape, with or without a carrier. In addition, the invention provides methods to identify such immunologically active molecules.

Progress in immunobiology has identified the essential immunological factors for the development of immune modulators, including the requirement for inducing innate and adaptive immune responses that control pathogens.

With the advent of widespread antibiotics resistance, immune modulators can be the most effective approach to deliver long-lasting protection against microorganisms including intracellular pathogens. The current focus on immune modulators requires the development of novel vectors, effective carriers and adjuvant systems.

As pathogens can also induce Th2 response and tolerance, this understanding may be used for the development of immune modulators for autoimmune diseases, transplantation and other medical applications. Most pathogens enter the body through the skin and mucosal membranes. Therefore these routes of administration are particularly well suited for immune modulation against infections entering through the skin, the airways, the gastrointestinal tract, or the sexual organs. Traditional vaccines are administered parenterally, far from the actual site of infection and their mucosal response is less pronounced.

It is now apparent that besides Toll-like receptors (TLRs) there are other receptors and pathways that play an important role in the innate immune response. An example for this is the nucleotide-oligomerization domain (NOD) proteins that recognize microbial motifs of intracellular microorganisms. Mindin, an extracellular matrix protein is also a mediator of inflammatory response to several bacterial surface components. These and other studies suggest that innate immunity involves additional factors independent of TLR signaling and that production of NFκB or IL-1 may not be sufficient to control infections.

Typical elements of innate immunity involved in controlling infections are: (1) proinflammatory response: NFκB mediated, activates many agents of inflammation, overstimulation can result in shock; (2) cationic host defense peptides: increased production of peptides stimulated by bacterial pathogen associated molecular patterns (PAMPs) and signaling molecules; (3) phagocytic cell activation: increased intracellular killing in neutrophils and macrophages (both oxidative and non-oxidative mechanisms enhanced, increased cytokine production; (4) chemotaxis: increased endothelial adhesion of phagocytic cells, cell migration to the site of infection, diapedesis; (5) extracellular killing mechanism: complement activation, enhanced iron chelation, antimicrobial peptide secretion, production of degradative enzymes; (6) infection containment: clot formation via fibrinogen activation; (7) wound repair: fibroblast growth and adherence, angiogenesis; and (8) adaptive immune responses: B- and T-cell activation, often via dentritic cells.

Stimulation of innate immunity may be accomplished by using interferons, monophosphoryl-lipid A, imiquimod, CpG nucleotides or cationic peptides. Innate immunity however has a limited capacity to fend off infections and in such scenario the adaptive immune response takes over.

Recently it has been recognized that dendritic cells are essential to link the innate and adaptive immunity and this knowledge allowed immunologists to design immune modulation strategies against poorly immunogenic antigens. Dendritic cells (DC) originate from precursors of both the myeloid and lymphoid lineages, but are main antigen-presenting cells (APC). DCs are present in every tissue, and during an infection are the key immune cells to enter into contact with the invading pathogen. They are the bridge between the innate and the adaptive immune response.

Endothelial and epithelial cells, monocytes, macrophages and other cells, including immature DCs express pathogen pattern recognition receptors (TLR receptors, lectin domain receptors and other receptors) that bind conserved pathogen associated molecular structures (PAMPs for short) shared by the pathogens such as lipopolysaccharide from Gram negative bacteria, lipoteichoic acid from Gram positive bacteria, peptidoglycan, peptidoglycan-associated lipoproteins, bacterial DNA and flagellin from Gram negative and Gram positive bacteria as well as viral RNA. Different cells express different receptors allowing a tailored response to the pathogen. Upon activation, immature antigen-capturing DC differentiate into mature antigen-presenting DC, able to present antigen in the MHC class-II and class-I contexts, as well as up-regulate the expression of surface co-stimulatory molecules such as CD80 and CD86.

Mature and activated DC migrates to secondary lymphoid organs (lymph nodes, spleen, Peyer's patches), where they translocate to the T-cell areas. The interaction of DC with and stimulation of T-cells is dependent on cytokines, chemokines and adhesion molecules such as intercellular cell adhesion molecules (I-CAMs), leukocyte function associated molecule 1 (LFA-1) and dendritic cell specific ICAM grabbing nonintegrin (DC-SIGN).

Depending on the local cytokine environment and the antigen, cellular T-helper (Th1) and humoral antibody mediated Th2- or Treg-oriented immune responses are triggered to various degrees. The dose of antigen has been shown to direct the Th1/Th2 differentiation, with high doses stimulating preferentially the Th-1 response and low doses the Th-2 response. Carrier devices displaying antigenic proteins and DNA vaccines have been shown to be taken up by immature dendritic cells and lead to an immune response. DC therefore represents a main but not the only target of development for the modulation of the immune system.

Mucosal DCs specifically provide an important first-line of defense by ingesting foreign invaders via both pinocytosis and receptor-mediated endocytosis. DC plays a critical role in mucosal immunity as bodily mucosa act like a barrier between the inside and the outside of the body. DC can be found on the lining of the respiratory tract and of the gut. Langerhans' cells are a population of DC found in skin and mucosa. DCs and M cells transport antigens to the underlying lymphoid follicle that is the immune-inductive site of the gut. Similar nasal and bronchus associated lymphoid tissues have been described in the respiratory tract. This system is important in the gastrointestinal tract, but in the airways, the underlying DC network may be even more important.

In the case of oral administration, the immune modulator must pass undegraded through the stomach and the upper intestines. Such degradation is unlikely to occur through a nasal, ocular or genital route of administration. Subsequently, the immune modulator must be taken up through the intestinal epithelium, so it can be adsorbed and subsequently presented to the immune-competent cells by the antigen-presenting cells. The immune competent cells are located in the epithelium, the lamina propria or beneath the basal membrane. Therefore, the immune modulator components must be formulated with a carrier taking them through this barrier. When bound to particulate carriers, it is generally accepted that the molecules can be transported over the barrier by the M-cells in the Peyer's patches.

Premature breakdown or release of the bioactive molecules has hampered the development of particle-based vaccine and drug delivery technologies. This is the likely explanation why in the published literature a high dose of antigen/drug is still required to achieve comparable responses to the injected counterpart. Besides the poor utilization of antigens and drugs, the other main criticism refers to the poor capacity of M-cells in the Peyer's patches (PP) to transport particles and the insufficient immune and other responses induced in humans. The epithelial M-cells of the PP are known to allow the transport of certain bacteria, viruses and protozoa from the intestines. Several studies have shown that a size-dependent uptake with a maximal diameter of 10 μm may occur by M-cells, DCs and Caco-2 cells.

Recent information on the uptake of particles by M-cells and the different types of dendritic cells (DCs) present in the PPs and their vicinity may provide an understanding of the mechanisms involved. Beyer (Beyer T., et al; Bacterial carriers and virus-like-particles as antigen delivery devices: Role of dendritic cells in antigen presentation. Curr. Drug Targets-Infect. Disord, 2001 1, 287-302) followed the uptake and kinetics of Baker's yeast cells (*Saccharomyces cerevisiae*) into PP, assuming it as an inert model for transport through the mucosa. A typical time dependency compatible with the transport to different types of phagocytosing, antigen-processing macrophages or dendritic cells was found for the distribution of the yeast cells in the M-cells, the intercellular pocket below the M-cells and the space beneath the basal membrane. Depending on where the DCs are located, they were found to have different functions in the PP microenvironment producing Th1 or Th2-directing cytokines upon activation. The cytokine and chemokine microenvironment will then subsequently decide the differentiation of the Th-cells to Th1 and Th2 subsets, respectively and affect the survival or apoptosis of T-cells, as well.

In addition, the differentiation of the B-cells and the homing of the mucosal plasma cells are regulated by separate cytokines (IL-6 in addition to TGF-β, IL-4, IL-5, and IL-10) and the specific homing receptor, $a_4b_7$. It can thus be concluded that there seem to be mechanisms available in the mucosa, by which mucosal modulation of the immune system can induce a more differentiated immune response, better mimicking the response to a natural infection than obtained by other routes of administration.

Although much has been learned about DC, their precursors and various DC subtypes that have been proposed, the full degree of functional complexity and plasticity of DC renders difficult predictions about the effect of a specific vaccine on DCs and subsequent Th1, Th2 and Treg responses. However, some of the results obtained for DC matured in vitro might be extrapolated to mature DC isolated from the lymphoid organs since they display similar characteristics (Shortman K, et al; Mouse and human dentritic cell subtypes. Nat. Rev. Immunol. 2002 March 2(3): 151-61). For instance, the potential of the *mycoplasma* lipopeptide MALP-2 to modulate DC response has been studied in vitro (Weigt H., et al; Synthetic *mycoplasma*-derived lipopeptide MALP-2 induces maturation and function of dendritic cells. Immunobiology 2003, 207(3): 223-33). MALP-2 treatment of DC induced the expression of CD80, CD86 and the release of bioactive TNF-α and IL-10, as well as the proliferation of autologous lymphocytes and the production of IL-4, IL-5 and γ-INF by the latter. These features correlate with an ability to stimulate T-cells and therefore suggest a possible effect of MALP-2 on DC in vivo.

Synthetic carriers may enable the immunostimulating effect of antigens for MHC Class I and II presentation. Synthetic carriers may be developed into a versatile system that can be tailored to a variety of potential applications. The character of these carriers can significantly influence the outcome and efficiency of the immune response. Synthetic carriers, such as particles may ease the hurdles of quality assurance and validation in vaccine development and production, and thus shorten the time for approval and to the market.

Several immune stimulatory components (peptides, proteins, lipids or polysaccharides) of different infectious microorganisms can be used for vaccination. These components can be synthesized, purified from the microorganisms or produced by recombinant DNA technology. However, they require suitable adjuvants when administered in free, soluble form orally or parenterally.

[Several particle-based systems have been tested as carriers for various antigens and drugs. Chitosan, poly-DL-lactic acid, or polyacryl starch micro particles have previously been described as a drug carrier system. Examples of such systems are described in U.S. Pat. Nos. 5,603,960 and 6,521,431. In one report, it was observed that starch micro-particles with covalently bound human serum albumin (HSA), as a model antigen functioned as a strong adjuvant in mice when administered parenterally and the micro particles alone were not immunogenic.

It should be pointed out, though, that the uptake is most likely dependent on the structure and the possible adhesive properties of the carrier, too. Agarose and other polysaccharides have intrinsic mucoadhesive properties, which may improve their interaction with different mucosal membranes and facilitate uptake.

SUMMARY OF THE INVENTION

Pursuant to this invention, new compositions are described for an immunologically active composition or compositions that can induce protective immunity or tolerance. The composition to induce protective immunity both in uninfected or infected host consists of antigenic epitopes but excludes or eliminates epitopes that participate in immune "escape" or induce tolerance. Protective immunity can be induced also by a composition that include a pathogen associated molecular pattern(s) and/or a carrier with or without the antigenic epitopes. Another immunologically active composition that induces tolerance includes an escape epitope(s) or a molecular pattern(s) important for pathogen escape with or without a carrier. In addition the invention provides methods to identify such immunologically active molecules. A suitable example is pathogen associated molecular pattern (PAMPs) recognition molecules with or without modified mycoplasmal antigens attached. Such molecular compositions appear to modulate anti-mycoplasmal immune responses in both uninfected and infected hosts. Some of the antigens induced tolerance or immune escape.

Accordingly, one aspect of the present invention is an immunologically active composition to induce protective immunity, the composition comprising:

(1) at least one pathogen associated molecular pattern;

(2) optionally, at least one immune active antigen or antigenic epitope; and (3) at least one carrier effective to deliver the composition to an organism so that protective immunity is induced thereby.

In many cases, it is desirable to include the at least one immune active antigen or antigenic epitope. Suitable examples are described further below. Typically, the at least one immune active antigenic epitope is devoid of escape epitopes. This is important for preventing selection pressure that would otherwise lead to the evolution of pathogens whose replication is not blocked by the immune response. An example of a pathogen for which selection pressure is likely to be important is the influenza virus, which rapidly mutates, so much so that a new vaccine needs to be prepared for each influenza season to provide immunity to the particular strain or strains of influenza likely to cause human disease. Another example of a pathogen for which selection pressure is likely to be important is the human immunodeficiency virus (HIV), which also mutates rapidly.

Another aspect of the present invention is an immunologically active composition to induce tolerance, the composition comprising:

(a) at least one pathogen associated molecular pattern;

(b) at least one immune active antigen or antigenic epitope; and (c) at least one carrier effective to deliver the composition to an organism so that tolerance is induced thereby.

Typically, the immune active antigenic epitope is a peptide, protein, a recombinant peptide or multi-peptide, a recombinant protein, lipid, carbohydrate, nucleic acid or other bioactive molecule or a combination of any of these. Typically, if the immune active antigenic epitope is a peptide or protein, the peptide or protein possesses immune modulatory posttranscriptional modulations. Typically, the posttranscriptional modulations involve carbohydrate and/or lipid moieties. Typically, the posttranscriptional modulations contain terminal mannosylation; in this alternative, typically, the immune modulatory terminally mannosylated substances are depleted from the immune protective composition. They can be depleted by an oxidative step, by enzymatic treatment, or by sugar-specific affinity binding. Alternatively, the posttranscriptional modulations involve lipid moieties and the lipid moieties are removed by delipidation.

Typically, the immune active antigenic epitope is a peptide or protein and the immune active peptide or protein has no immune modulatory posttranscriptional modifications. Also, typically, the immune active peptide or protein does not possess amino acid sequences capable of N-glycosylation and/or lipoylation. In another preferred alternative, the immune active antigenic epitope is a peptide or protein and the immune active protein or peptide possesses amino acid sequences capable of binding cell surface glycosaminoglycans (GAGS). Typically, these the amino acid sequences are polybasic in nature and of the general formula of XBBXBX, XBBBXXBX, BBXXBBBXXBB, BBBXXB, BXBXB, BBB, BXBXXXBXB, or BXBXXXXXBXB, wherein B is a basic amino acid and X is any other amino acid. Typically, the GAG binding amino acid sequences are used to generate antibodies to the peptide or protein that are capable of interfering with pathogen binding to cell surfaces. The GAG can be selected from the group consisting of heparin and its analogues. The immune active antigenic peptide or protein can possess complement activating activity, alone or in combination with antibodies. The immune active antigenic epitope can be a plurality of peptides that are combined into a single multi-peptide. The immune active antigenic epitopes can include both T-cell epitopes and B-cell epitopes.

Typically, the pathogen associated molecular pattern is selected from the group consisting of:

(1) a TLR 1 receptor agonist;

(2) a TLR 2 receptor agonist;

(3) a TLR 3 receptor agonist;

(4) a TLR 4 receptor agonist;

(5) a TLR 5 receptor agonist;

(6) a TLR 6 receptor agonist;

(7) a TLR 7 receptor agonist;

(8) a TLR 8 receptor agonist;

(9) a, TLR 9 receptor agonist;

(10) a NOD-1 agonist;

(11) a NOD-2 agonist;

(12) DC-SIGN;

(13) L-SIGN; and

(14) a mannose receptor.

When the pathogen associated molecular pattern is a NOD-1 agonist or a NOD-2 agonist, the NOD-1 agonist or NOD-2 agonist can be selected from the group consisting of bacterial peptidoglycan and a derivative of bacterial peptidoglycan.

Another aspect of the present invention is a method for identifying immune active peptides capable of interfering with glycosaminoglycan binding of pathogens comprising the steps of:

(1) performing heparin adsorption;

(2) performing immunoaffinity selection; and (3) optionally, performing proteolytic digestion of a protein or proteins isolated by immunoaffinity selection to generate immune active peptides. Immunoaffinity selection can be carried out by methods well known in the art and described, for example, in G. T. Hermanson et al., "Immobilized Affinity Ligand Techniques" (Academic Press, Inc., San Diego, 1992); other methods are also known in the art.

Yet another aspect of the present invention is a method for identifying immune active peptides capable of interfering with glycosaminoglycan binding of pathogens comprising analyzing sequence data using a bioinformatics analysis method utilizing polybasic linear motifs.

Still another aspect of the present invention is a method for identifying complement activating immune active peptides comprising the steps of:

(1) performing binding of complement fixing antibodies to a complement protein;

(2) using the antibodies for immunoaffinity selection of protein antigens; and (3) optionally, performing proteolytic digestion of the isolated protein antigens.

Immune active peptides produced by these methods are also aspects of the invention. Additionally, a protective antibody can be based on the identified immune active peptide for overcoming disease in host organisms.

In compositions as described above, the molecules can be present as a mixture. Alternatively, the molecules can be chemically linked together. The carrier is typically a microparticle. Preferably, the microparticles have a narrow size distribution range and are porous. Typically, the microparticles are less than about 10 µm in diameter; more typically, the microparticles are less than about 5 µm in diameter. Typically, the microparticles are made of a biopolymer. In one alternative, the immune active antigenic epitopes are noncovalently attached to the microparticles. In another alternative, the immune active antigenic epitopes are covalently attached to the microparticles. More than one immune active antigenic epitope and more than one pattern recognition receptor agonist can be associated with the microparticles. More than one pattern recognition receptor agonist can be associated with the microparticles.

Another aspect of the present invention is a method of eliciting an immune response in a subject comprising the step of administering an immunologically effective amount of a composition comprising at least one immune active antigenic epitope and at least one pathogen recognition (PR) receptor agonist associated with microparticles, wherein the microparticles are smaller than or in the same size range as a pathogen. The composition can comprise more than one pathogen recognition receptor agonist.

Yet another aspect of the invention is a method of in vivo delivery of an immunologically active composition in order to elicit an immune response in a subject comprising the step of administering an immunologically effective amount of a composition comprising at least one pathogen recognition (PR) receptor agonist associated with microparticles, wherein the microparticles are smaller than or in the same size range as a pathogen.

Still another aspect of the invention is a method of in vivo delivery of an immunologically active composition in order to elicit an immune response in a subject comprising the step of administering an immunologically effective amount of a composition comprising at least one immune active antigenic epitope and at least one pathogen recognition (PR) receptor agonist associated with microparticles, wherein the microparticles are smaller than or in the same size range as a pathogen.

Another aspect of the present invention is a method of eliciting a protective immune response to at least one pathogen comprising the step of administering, in a single dose or in multiple doses, an immunologically effective amount of a composition comprising one or more immune active antigenic epitopes and a combination of PR receptor agonists associated with microparticles, wherein said microparticles are smaller than or in the same size range as the pathogen and the immune response comprises Th1 or Th2 responses or a combination of both.

Yet another aspect of the present invention is a method of eliciting a protective immune response to at least one pathogen comprising the step of administering, in a single dose or in multiple doses, an immunologically effective amount of a composition comprising one or more immune active antigenic epitopes, excluding antigens that participate in immunological escape mechanisms, and a combination of PR receptor agonists associated with microparticles, wherein said microparticles are smaller than or in the same size range as the pathogen.

In administration or delivery methods according to the present invention, administration of the composition can occur via a mucosal route, a parenteral route, or a dermal route. Other routes of administration can alternatively be used.

In methods of inducing immunity according to the present invention, typically, the immune response interferes with glycosaminoglycan binding elements on a pathogenic microorganism.

Alternatively, compositions according to the present invention can be used in methods of inducing immunological tolerance. A method of eliciting tolerance to an immunologically active agent comprises the step of administering an immunologically effective amount of a composition comprising one or more immune active antigenic epitope and a combination of PRR agonist associated with microparticles, wherein the microparticles are smaller than or in the same size range as a pathogen and the immune response comprises the induction of a regulatory response or downregulation of immune functions or immune escape. The composition can include therein an immune active antigenic epitope having a lipid-containing moiety. The immunologically active lipid containing moiety can be attached to the microparticles independently of the immune active antigenic epitope. The immunologically active lipid containing moiety can have carbohydrate constituents; the carbohydrate constituents can be the result of N-glycosylation. The immune active antigenic epitope can comprise motifs including at least one amino acid selected from the group consisting of asparagine, threonine and serine wherein the motifs are Asp-X-Ser or Asp-X-Thr motifs, wherein X can be any amino acid except proline.

BRIEF DESCRIPTION OF THE DRAWINGS

The following invention will become better understood with reference to the specification, appended claims, and accompanying drawings, where:

DESCRIPTION OF THE PREFERRED EMBODIMENT

Figure 1:
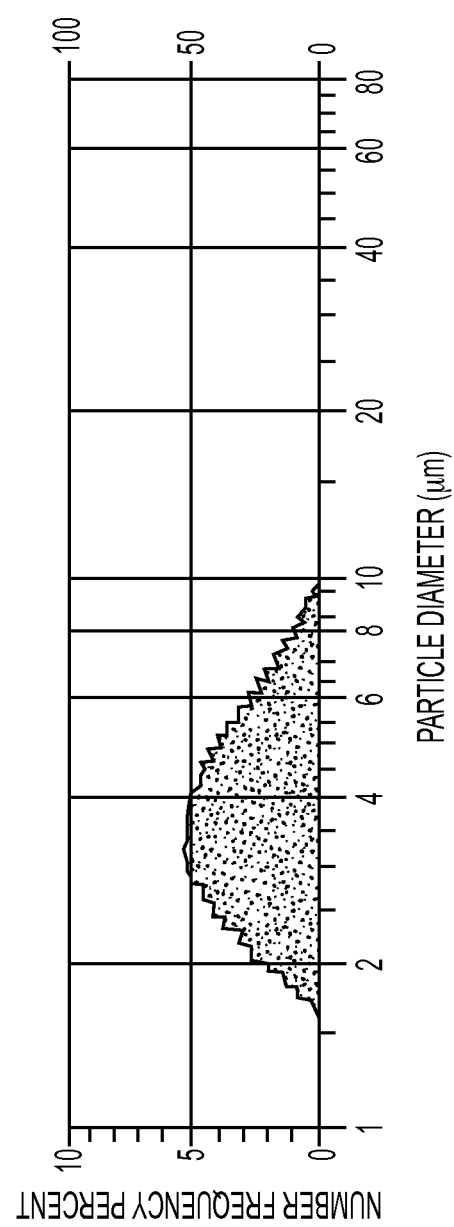
FIG. 1 is a graph showing the particle distribution of agarose microparticles suitable for use in microparticle carrier compositions according to the present invention (Example 1)

This invention describes immunologically active compositions, methods of targeting molecules to certain cell population and eliciting responses in an animal model and methods of producing the subject compositions.

There is a need to produce more effective immune modulatory agents and delivery vehicles for a number of diseases or conditions as well as for protection from pathogens against which vaccines are currently unavailable or ineffective.

Traditional vaccines using attenuated, killed or genetically modified pathogens are limited to the immune response that the molecular pattern of the pathogen and its interaction with the Pathogen Recognition Receptors (PRR) of the immune system determines. The successful pathogens that can establish chronic infections have molecular patterns that allow them to evade the body's immune response while other pathogens, such as influenza viruses, uses mutations (antigenic shift and drift) resulting in escapes such as production of antibodies that results in increased viral uptake to maintain themselves.

In general, pathogen-specific antibodies play an important role in the control of the infections in a number of ways. However, in some instances, the presence of specific antibodies can be beneficial to the pathogen. This activity is known as antibody-dependent enhancement (ADE) of infection. The ADE of infection is a phenomenon in which pathogen-specific antibodies enhance the entry of pathogen, and in some cases the replication of pathogen, such as viruses, into monocytes/macrophages and granulocytic cells through interaction with Fc receptors. This phenomenon has been reported in vitro and in vivo for pathogens representing numerous families and genera of public and veterinary health importance. These pathogens, such as *M. gallisepticum* share some common features such as preferential replication in macrophages, ability to establish persistence, and antigenic diversity.

For some pathogens, ADE of infection has become a great concern to disease control by vaccination. Consequently, numerous approaches have been made to the development of vaccines with minimum or no risk for ADE. Identification of pathogen epitopes associated with ADE or neutralization is important for this purpose. In addition, clear understanding of the cellular events after pathogen entry through ADE has become crucial for developing efficient intervention. However, the mechanisms of ADE still remain to be better understood. Therefore, effective vaccines against these pathogens are difficult to develop. Therefore, we have identified motifs that were important for the protective immunity by interfering with important cell attachment mechanism and motifs that need to be excluded from a formulation in order to induce protective immunity without escape. We have also identified motifs that induced escape or tolerance.

We have investigated the possibility of targeting immunologically active molecules to certain cells by a carrier comprised of a polysaccharide, such as native agarose thereby achieving immune modulation of both innate and adaptive immune responses and protection from infection. This invention can obviously be used in other applications in which other receptors can be targeted using other particles, as well. Agarose has the advantage that it is a natural polysaccharide, a D-galactose polymer that is biodegradable and proven compatible with mammalian cells. Parenterally administered agarose micro-particles have been found to exhibit weak macrophage activating capacity and a comparable adjuvant property to aluminum hydroxide (Gronlund H. et al., Carbohydrate-based particles: a new adjuvant for allergen-specific immunotherapy. Immunology 2002 107, 523-529).

From an end-user point of view, it is important that the vaccine product requires no refrigerated storage and still has a long shelf-life. Agarose particles can meet these requirements. Also, it is important that the administration of vaccine or drug delivery vehicle be as simple as possible. This is why a needle-free, mucosally, especially orally administrable composition has advantage over parenterals. Oral applications, however, have been plagued with stability problems due the effects of the digestive system.

We have reasoned that antigens coupled to the porous agarose matrix might be protected from degradation inside the GI tract. The linkage between the ligands and the particles assures that the same antigen-processing cells take up the adjuvant and the antigen. Also, the size of the agarose microparticles (<5 μm) may make them suitable for allowing the particles to pass into the Peyer's patches (PPs).

The effectiveness of unmethylated CpG DNA, Poly I:C or MALP-2 as adjuvants suggests that pathogen associated molecular pattern (PAMPs) motifs, if co-immobilized with antigens, would target the uptake of immunologically active compositions at mucosal surfaces by different APCs expressing the appropriate PAMP receptors.

Various DC subsets and other immune competent cells have different pattern recognition receptors. Using a combination of ligands, the targeting of the appropriate subset of cells could be accomplished.

Therefore, we reasoned that receptor agonists (PAMP receptor) molecules, such as Toll-like receptor (TLR), lectin receptor or NOD receptor agonists should be co-immobilized along with bioactive molecules to the carrier. We reasoned that the attachment properties, the targeting and the uptake of immunologically active compositions may be improved as the immune system would be exposed to a designed, "synthetic microorganism" and this may significantly enhance the targeted uptake and efficacy of such immune modulators and a tailored immune response could be achieved. The tailored targeting could also improve the pharmacokinetics and reduce potential side effects of such designed immune modulators.

Toll-like receptors (TLRs) and NOD, lectin receptors, etc. are pathogen pattern recognition receptors for microorganism-derived molecules. They are the primary sensors of the innate and adaptive immune systems. There are 10 TLRs (TLR 1-10) currently identified. Each recognizes one or more specific ligand and performs signal transduction. Newly discovered receptors and receptor interactions are regularly found to be involved in cell activation by bacterial products. Evidence is accumulating that cooperation between these receptors comes into play to refine ligand discrimination and specificity of response. Clustering of receptors in lipid rafts has also been found after ligand binding. Such studies also revealed myeloid differentiation primary response gene 88 (MyD88)-dependent and independent pathways.

Each TLR is a type-I transmembrane receptor that has an extracellular leucine-rich domain and an intracellular portion that contains a conserved region called the Toll/IL-1R homology (TIR) domain, that upon activation results in the recruitment of the MyD88 protein in MyD88-dependent forms of signaling. Some microbial pathogens can also be endocytosed and exert their activity directly in the cytoplasm, using the leucine-rich domain of TLRs, NOD-1 and NOD-2 as is the case, for example, in intracellular Gram-positive bacterial peptidoglycan sensing. However, these various pathways seem to converge towards the nuclear translocation of NF-κβ and activation of inflammatory genes and production of different cytokines. The ligation of TLRs 7, 8 and 9 results in IFN-α and IL-12p70, eliciting strong Th1 response with cross presentation/CTL. The activation of TLR 3 results in INF-α and Th1 response, while TLR5 induces Th1 through IL-12p70 and TLR4 induces Th1 through IL-12p70 and INF-α production, all leading to cross presentation/CTL. However, the ligation of TLRs 1, 2 and 6 induces weak IL-12p70 response with high IL-10 levels and along with some other PRR (pathogen recognition receptor), such as DC-SIGN results in Th0/Th2/TReg responses.

TLR-4 has been the most widely studied of this family of receptors. It is known to recognize lipopolysaccharide from Gram-negative bacteria and lipoteichoic acid from Gram-positive bacteria, whereas TLR-2 binds bacterial lipoproteins/lipopeptides, mycobacterial or mycoplasmal components.

The Lps2 mutation identified the role of TIR resistance adaptor protein (TIRAP) in the TLR-3 and TLR-4 MyD88-independent pathway. TIRAP has been discovered as another intracellular player downstream of TLR-2 and TLR-4. A MyD88 independent pathway was also shown to be involved in the regulation of LPS-mediated maturation of DC. TLR-1 and TLR-6 are known to function as the other part of a heterodimer with the TLR-2 receptor.

TLR-3 recognizes double-stranded viral RNA. TLR-5 was identified as the receptor for flagellin from Gram negative and positive bacteria, and signaled through MyD88. TLR-7 responds to single stranded RNA and small synthetic immune modifiers such as imiquimod, R-848, bropirimine and loxoribine. TLR-9 is known to detect unmethylated bacterial DNA. CpG DNA oligonucleotides are currently being investigated for their ability to serve as adjuvant and stimulate human dendritic cells for vaccine development.

TLR-4, TLR-7 and TLR-9 are particularly important with regard to vaccine development. Human TLR-8 was recently identified as a receptor for single stranded RNA and for resiquimod (R-848). TLR-7, TLR 8 and TLR-9 have recently been proposed to be considered as a subgroup in the TLR receptor family in that their ligands are recognized in endosomal/lysosomal compartments.

C-type (Calcium dependent) lectin receptors (CLRs) are also expressed and these bind to conserved oligosaccharides that are commonly found on the surface glycoproteins of viruses, bacteria and other pathogens. CLRs expressed by DCs include the mannose receptor (CD206), DEC-205 (CD205), Langerin (CD207) and DC-specific intercellular adhesion molecule 3-grabbing nonintegrin (DC-SIGN; CD209). These receptors differ not only in their expression on various subsets of DCs and other tissues but they also recognize different oligosaccharides thus discriminating between different ligands.

DC-SIGN is a 44 kDa type II transmembrane protein that binds and internalizes several viruses such as HIV, Ebola virus, CMV, Dengue virus, hepatitis C virus and bacteria, such as Mycobacteria though other receptors are also involved. Other pathogens can also interact with DC-SIGN. It is very important in the function of DC, both in mediating naive T cell interactions through ICAM-3 and as a rolling receptor that mediates the DC-specific ICAM-2-dependent migration processes.

The collaboration between TLR and other immune-recognition receptors has been described. An example of this is the collaborative determination of inflammatory responses by dectin-1 and TLR2. Complex particles such as yeast cell walls are recognized by multiple innate immune receptors including TLR2-TLR6, dectin-1 and CD14. TLR2-TLR6 heterodimers activate NF-κB and the production of chemokines and cytokines such as TNF-α. Dectin-1 recognizes α-glucans in the cell wall and triggers phagocytosis as well as activating reactive oxygen production by the NADPH-oxidase. In addition, dectin-1 signaling combines with TLR2-TLR6 signaling to enhance production of specific cytokines, such as IL-12.

Because of the cooperation between TLR receptors and with other receptors and the interactions between intracellular molecular downstream mechanisms, it was not surprising to observe synergistic effects between microbial pathogenic compounds such as lipoteichoic acid, CpG DNA and peptidoglycan, suggesting that the effect of TLR activators as adjuvants may be amplified when used in combinations in the development of immune modulators.

The co-immobilization of appropriate PRR (pathogen recognition receptors) ligand with a bioactive molecule may allow the targeted modulation of immune response leading to a strong cellular response (under relatively stronger Th1 influence) and/or humoral response (under Th2 influence). Alternatively, when immunized with a different composition, immune tolerance can be obtained.

It might be possible that a strong cellular response would be induced even in the presence of an established humoral immunity or tolerance. This way we may anticipate the development of an immune modulator that is efficient both in uninfected and infected hosts. Such result would greatly enhance the utility of vaccination.

We have established in a chicken model system that a significant degree of protection can be achieved against the infectious strain of *Mycoplasma gallisepticum* when the animals were vaccinated prior to mycoplasmal challenge. In addition, the reversal of characteristic pathological symptoms was also observed on pre-infected animals indicating that such vaccine is effective to treat an infected flock. This is significant because of the widespread antibiotic resistance of various strains of microorganisms and the growing public and regulatory concerns about allowing the use of antibiotics prophylactically in farm animals. In addition, we have found that just a very small amount of antigen (10 μg) per animal was necessary to elicit a protective response by this method as opposed to over 100 μg described in the literature using microparticles that had incorporated the antigen. (Brayden, D. 2001 European Journal of Pharmaceutical Sciences 14:183-189). This suggests that the immune modulator molecule(s) is not degraded while traversing the gut in the animals and that it is delivered to the targeted mucosal immune cell in an efficacious manner. This is a significant improvement over existing immunologically active compositions.

However with escalating antigen doses a reduction in the protective effect was observed suggesting the presence of an immune suppressing component among the immunoaffinity purified antigens. DC-SIGN has been implicated in the escape mechanism of pathogens. DC-SIGN is a C-type lectin specific for high-mannose containing lipid molecules. *Mycoplasma* membranes are composed of high proportions of lipids and different *mycoplasmas* have been shown to bind the Concanavalin A affinity resin, indicating the presence of mannose on the *mycoplasma* surface. We hypothesized that molecules participating in immunological escape including posttranscriptional N-glycosylated molecules including posttranscriptional lipomannan modification on a purified protein(s) containing terminal mannose moieties may mediate this effect. The removal of terminal mannoses by enzymatic digestion or chemical breakdown was subsequently attempted. In addition, terminally mannosylated lipoproteins were adsorbed out on a mannose specific immobilized lectin—Concanavalin A (ConA) column.

The ConA column retained about one-third of the constituents of the purified antigen and the vaccine prepared by this antigen exhibited the highest protective effect and a linear dose-response with increasing antigen concentration. On the other hand, the antigen recovered from the Con A column caused a suppression of the inflammatory reaction in the animals while a very high level of pathogen presence was found in their internal organs. It seems that these mannosylated components of *M. gallisepticum* are participating in the escape mechanism of this pathogen, resulting in immune suppression and the development of tolerance to the pathogen. We have also demonstrated that proper antigen characteristics can help to shift the immune response towards either protection or tolerance. This confirmed our hypothesis and also supports the observation made with the immobilized mycoplasmal membranes that lipomannan posttranscriptional modifications may induce pathogen tolerance in the host. This understanding can now be utilized to prepare immune modulatory microparticles endowed with the property of potentially inducing tolerance or suppressing existing immune responses. Lipid post-transcriptional modification of antigens also plays a role in developing tolerance to pathogens. Therefore, we have also attempted deacylation of purified antigens that proved efficacious, confirming the role of lipids in the pathomechanism of *mycoplasmas*.

The main conclusion from these experiments is that an epitope vaccine derived from the analysis of native proteins should not contain epitopes rich in amino acids that can undergo glycosylation and/or lipoylation (Asn, Thr, Ser) if one wants to achieve protective immunity while ligands incorporating these amino acid motifs could be used to induce tolerance. This provides multiple uses for compositions and methods according to the present invention.

In subsequent studies, we have used the blood and sera from the vaccinated protected animals in order to identify antigenic epitopes that were responsible for the protection. This way we have focused on developing the scientific bases for an epitope-based vaccine as large-scale production of *mycoplasma* as well as the purification of antigenic proteins could be cost-prohibitive for many applications. In a previous study, we have shown that various *mycoplasmas* are capable of binding to heparin and heparin analogues (Szathmary, S. et al.: Binding of *mycoplasmas* to solid phase adsorbents. Acta Vet Hung 2005, 53(3):299-307). Glycosaminoglycans (GAGs) are expressed on the surface of mammalian cells and glycosaminoglycan binding proteins on the surface of pathogens mediate adhesion to target cells (Wadstrom T, Ljungh A: Glycosaminoglycan-binding microbial proteins in tissue adhesion and invasion: key events in microbial pathogenicity. J Med Microbial 1999, 48(3):223-233). Consensus sequences of several types have been reported, characterized by predominantly basic amino acids in a region: XBBXBX, XBBBXXBX, BBXXBBBXXBB, BBBXXB, BXBXB, BBB, BXBXXXBXB, or BXBXXXXXBXB where B is a basic amino acid and X is any other amino acid. Another way to look at this is that linear basic motifs are involved in the mechanism of pathogenicity. These sequences are essential for attachment which probably serves as an initial step in the mechanism of mucosal entry by pathogens. Therefore, the neutralization of this capability could prevent infection and possibly allow the development of broad-spectrum therapies against a variety of pathogenic microorganisms. This possibility has not been recognized earlier as a basis for vaccine development. We reasoned that antigenic epitopes adjacent or sterically close to GAG binding domains could be neutralizing and raised the possibility that such binding sites could possibly be incorporated within neutralizing epitopes.

Therefore, we proceeded with the isolation of heparin binding proteins from *M. gallisepticum* using affinity chromatography on Heparin Actigel resin (Sterogene Bioseparations, Inc., Carlsbad, Calif.). Subsequently, we have purified IgG from neutralizing sera obtained from vaccinated chickens against *M gallisepticum*. The purified IgG was immobilized to the activated resin Actigel ALD (Sterogene Bioseparations, Inc., Carlsbad, Calif.) and the isolated heparin binding proteins were adsorbed to the column. Bound proteins were digested by adding trypsin to the column and peptide fragments containing immunogenic epitopes including heparin binding sequences were eluted and analyzed by MALDI-MS in order to obtain sequence information. IgGs purified using such antigenic epitopes or monoclonal antibodies against such epitopes when administered in vivo can also confer protective immunity on infected hosts. Alternatively, other proteolytic enzymes known in the art, such as chymotrypsin, elastase, bromelain, V-8 protease, pepsin, and thermolysin can be used in place of trypsin.

In parallel experiments, we have re-adsorbed isolated heparin binding proteins to Heparin Actigel and carried out similar tryptic digestion of bound proteins. The fragments recovered from the resin were also analyzed by MALDI-MS for sequence information.

It is also important to identify epitopes participating in opso-phagocytosis, which utilizes the complement system. Specifically, complement fixing antibodies are purified from the vaccinated chicken sera on an immobilized C1q column and such antibodies are used for the identification of epitopes capable of inducing such response. The purified IgG is subsequently immobilized and used to capture protein antigens from crude MG lysate. The bound proteins are digested with a protease while on the column and epitope sequences eluted and analyzed by MALDI-MS in order to obtain sequence information. IgGs purified using such antigenic epitopes or monoclonal antibodies against such epitopes when administered in vivo can also confer protective immunity on infected hosts.

A major problem with some of the current microorganism-based vaccines is the co-administration of immune stimulating and immune suppressive epitopes along with the mixture of PRR agonists present on the pathogen itself, some of which induce Th1, some Th2 or Treg responses. These vaccines do not overcome the persistence of various infectious agents in the host and can turn it into a "pathogen factory" in the absence of a clinical disease. This approach may even apply a selection pressure on the pathogens and can lead to the development of more virulent strains. In contrast, our strategy was the creation of an artificial "pathogen-mimicking" microparticle that contains just the immune stimulating epitopes, while excluding epitopes and/or PRR agonists that participates in the pathogen's escape from the immune system, along with suitable immune response-directing PRR agonist molecules. The identified epitopes can also be combined into a single multi-peptide presenting splicing sequences or linkers between the particular antigenic epitope peptides. By this approach the distorted immune response caused by persistent pathogens is overcome and a balanced mix of cellular and humoral immune response is developed that leads to the eradication of infectious agents. The escape epitopes or PRR agonists could be utilized for the development of tolerance when necessary to override an undesired autoimmune reaction.

Typically, the biologically active molecule is a molecule that is active with the immune system, such as an immunogen or another molecule that modulates immune function, such as an immune stimulator, an immune inhibitor, or an agent that induces immunological tolerance.

The bioactive molecule can be non-covalently or covalently attached to the microparticles. Methods for covalent attachment are known in the art and are described for example, in P. Tijssen, "Practice and Theory of Enzyme Immunoassays" (Elsevier, Amsterdam, 1985, pp. 283-289, in S. S. Wong, "Chemistry of Protein Conjugation and Crosslinking" (CRC Press, Boca Raton, Fla., 1993), in T. E. Creighton, ed., "Protein Function: A Practical Approach" (IRL Press, Oxford, 1989), and in G. T. Hermanson, "Bioconjugate Techniques" (Academic Press, San Diego, 1996), all of which are incorporated herein by reference. Typically, when the microparticles are agarose, the bioactive molecule is attached to a hydroxyl group of the agarose. In general, the hydroxyl residues of polysaccharides can be activated by certain compounds that form intermediate reactive derivatives containing good leaving groups for subsequent nucleophilic substitution. Reaction of these activated hydroxyls with nucleophiles such as amines (for example, lysine groups in proteins or peptides) results in stable covalent bonds that crosslink the bioactive molecule to the agarose. Suitable reagents include carbonyldilmidazole, chloroformate derivatives, tresyl chloride, tosyl chloride, cyanogen bromide, divinylsulfone, cyanuric chloride, and bis-epoxides. Alternatively, the hydroxyl groups of carbohydrates such as agarose can be modified with chloroacetic acid to create a carboxylate functional group. As another alternative, amine functional groups can be created on polysaccharides; the reducing ends of carbohydrate molecules or generated aldehydes can be reacted with diamine compounds of low chain length (i.e., typically less than about 6 carbon atoms in the chain) to yield short alkylamine spacers that can be used for subsequent conjugation reactions. Hydrazide groups can be similarly created using bis-hydrazide compounds. The resulting functional group can then be coupled to the bioactive molecule using various reactions. For example, if carboxyl groups are generated, they can then be conjugated to proteins or peptides via the mixed anhydride method, the carbodiimide method, using dicyclohexylcarbodiimide, and the N-hydroxysuccinimide ester method. Aliphatic amines can be conjugated to proteins or peptides by various methods, including carbodiimide, tolylene-2,4-diisocyanate, or malemide compounds, particularly the N-hydroxysuccinimide esters of malemide derivatives. An example of such a compound is 4-(N-maleimidomethyl)-cyclohexane-1-carboxylic acid. Another example is m-maleimidobenzoyl-N-hydroxysuccinimide ester. Still another reagent that can be used is N-succinimidyl-3-(2-pyridyldithio) propionate. Also, bifunctional esters, such as dimethylpimelimidate, dimethyladipimidate, or dimethylsuberimidate, can be used to couple amino-group-containing moieties to proteins. Other methods for covalent linkage of compounds, including peptides, proteins, and carbohydrates, as well as other compounds, to solid supports are known in the art. Methods for noncovalent attachment depend on multiple noncovalent interactions such as hydrogen bonds, hydrophobic bonds, and salt linkages that can stabilize the interaction.

Typically, the biologically active molecule is one or more of a peptide, protein, recombinant peptide, recombinant protein, lipid, carbohydrate, nucleic acid, glycoprotein, or glycolipid. Combinations of these can also be used so that multiple biologically active molecules are attached to the same microparticles.

If the immune active molecule is a peptide or protein, it can have undergone immune modulatory post-transcriptional modifications. Typically, these involve sugar and/or lipid moieties. An example is terminal mannosylation. However, other sugar residues can be added to proteins or peptides. Alternatively, the immune active molecule can be isolated in such a way that the preparation of the immune active molecule is substantially depleted in terminally mannosylated molecules. This depletion can be undertaken by an oxidative step such as periodate oxidation, by enzymatic treatment, typically with hydrolytic enzymes, or by sugar specific affinity binding and subsequent purification of the depleted fraction. Other methods for depletion of terminal mannosyl residues are also known in the art.

Similarly, the immune active molecule can be isolated in such a way that the preparation of the immune active molecule is substantially depleted in lipid containing immune modulatory post-transcriptional moieties. This can be done by chemical hydrolysis or by coprecipitation with pentadecanoic acid. Alternatively, the lipid containing immune modulatory posttranscriptional moieties can be blocked with a charged detergent. A particularly suitable detergent is cetyl trimethyl ammonium chloride. Similar quaternary ammonium detergents can alternatively be used.

The optionally present target molecule is typically a pathogen pattern recognition molecule. In one alternative, the pathogen pattern recognition molecule is a TLR receptor agonist, such as a TLR1 receptor agonist, TLR2 receptor agonist, TLR3 receptor agonist, TLR4 receptor agonist, TLR5 receptor agonist, TLR6 receptor agonist, TLR7 receptor agonist, TLR8 receptor agonist, or TLR9 receptor agonist. In another alternative, the pathogen pattern recognition molecule is a NOD protein agonist such as a NOD-1 agonist or NOD-2 agonist. Typically, the NOD protein agonist is bacterial peptidoglycan or a derivative of bacterial peptidoglycan.

More than one biologically active molecule, such as an immune active molecule, and more than one pathogen pattern recognition molecule, where present, can be incorporated in the composition and stably associated with the microparticles.

Another aspect of the present invention is a method of eliciting an immune response in a subject by administering an immunologically effective amount of a composition as described above to the subject. Typically, the composition also includes the target molecule, such as the pathogen pattern recognition molecule. More than one immune active molecule and more than one pathogen pattern recognition molecule can be incorporated in the composition.

Yet another aspect of the present invention is a method of in vivo delivery of an immunologically active composition comprising administering an effective amount of a composition as described above to an organism that has an active immune system. Again, more than one immune active molecule and more than one pathogen pattern recognition molecule can be incorporated in the composition. The in vivo delivery of the immunologically active composition can be via mucosal surfaces, the parenteral route, the dermal route, or the subcutaneous route. Other routes of administration, can be used.

Still another aspect of the present invention is a method of eliciting a protective immune response to at least one pathogen comprising administering an immunologically effective amount of a composition comprising one or more immunologically active molecules (i.e., immunogens) and a combination of TLR receptor agonists stably associated with microparticles as described above to a subject to induce the protective immune response to the pathogen in the subject. The protective immune response comprises Th1 or Th2 responses or a combination of both Th1 and Th2 responses. Administration can be by means of a single dose or multiple doses.

Yet another aspect of the present invention is a method of eliciting tolerance to an immunologically active agent comprising administering an immunologically effective amount of a composition comprising one or more immunologically active molecules (i.e., immunogens) and a combination of TLR receptor agonists and NOD protein agonists stably associated with the microparticles to a subject to induce tolerance to the immunologically active agent in the subject. The immunologically active molecules can have a lipid containing moiety, which can be attached to the microparticles independently of the remainder of the immunologically active molecules. Alternatively, the immunologically active lipid containing moiety can further comprise carbohydrate groups.

Toxicity and therapeutic efficacy of compositions according to the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans or in other animals. The dosage of such compositions lies preferably within a range of circulating concentrations that include the $ED_{50}$ with little or no toxicity. The dosage may vary within this range depending upon the dosage form employed and the route of administration utilized.

For any compositions according to the present invention the therapeutically effective dose can be estimated initially from cell culture assays. For example, a dose can be formulated in animal models to achieve a circulating plasma concentration range that includes the $IC_{50}$ as determined in cell culture (i.e., the concentration of the test composition which achieves a half-maximal response with respect to the effect of the composition upon the immune system parameter being measured). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps the dose frequency, will also vary according to the age, body weight, and response of the individual patient. A program comparable to that discussed above may be used in veterinary medicine.

Use of pharmaceutically acceptable carriers to formulate the compositions herein described for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compositions can be formulated readily using pharmaceutically acceptable carriers well known in the art into dosages suitable for mucosal or subcutaneous administration.

The invention is illustrated by the following Examples. These Examples are included for illustrative purposes only, and are not intended to limit the invention.

Example 1

Selection of Microparticles

Agarose microparticles in the 1-10 μm ranges have been produced by Sterogene Bioseparations, Inc. (Carlsbad, Calif.) and tested using a Saturn DigiSizer 5200 (Micromeritis Instrument Corp). The data shown in FIG. 1 shows that the particle distribution is 75% is below 5 μm, 24% is 5-10 μm and 1% is above 10 μm.

Example 2

Culture of *Mycoplasma gallisepticum* (MG)

To 0.1 ml of *mycoplasma* growth medium the lyophilized form of *M. gallisepticum* (K781R-16P) was added and placed into 1.5 mL of culture medium in an incubator at 37° C. Growth of *mycoplasma* was monitored by color change (pink to orange or yellow) or by plating on agar plates and checking the colonies. Large volumes (10-15 L) of *Mycoplasma* cultures were grown by transferring infected cultures to fresh media. Subsequently, the cultures were centrifuged at 5500 rpm for 30 min. Washing of the pellet with PBS was performed (20 min at 5500 rpm) until the $OD_{280}$ of the supernatant was below 0.2. The pellet was re-suspended in 20 mL of PBS.

Example 3

Preparation of Immunoaffinity Column for MG Antigen Purification

Step 1:

To 64 ml of anti-*M. gallisepticum* chicken serum, 128 mL deionized (DI) water was added in a glass beaker. The pH of the solution was adjusted to 4.5 using glacial acetic acid. The solution was stirred rapidly but care was taken to avoid splashing or foaming. CAP-8 Precipitating Solution (Sterogene Bioseparations, Inc. Carlsbad, Calif.) was vigorously shaken for 10 minutes. Subsequently, 64 ml of CAP-8 Precipitating Solution was measured out and slowly added to the sidewall of the vortex formed by stirring over a period of 1 to 2 minutes. The stirring was then slowed down to a rate just moving the solution. The solution was stirred for 30 minutes at room temperature and then transferred to an appropriately sized centrifuge tube and precipitate spun down at 5,500 rpm for 15 minutes. The supernatant was decanted into a container and the pellet washed once with 20 mL of 20 mM Na acetate, pH 4.8 buffer. The supernatant was filtered by using an 0.22 μm syringe filter.

Step 2:

The SP Thruput Plus cation exchange resin (Sterogene Bioseparations, Inc. Carlsbad, Calif.) was suspended in 3 bed volumes of 1M NaOH for 10 minutes and then washed with DI water to neutrality. Subsequently, it was washed with 10 bed volumes of 0.5 M sodium acetate, pH 4.8 and then with 20 bed volumes of DI water. The resin was equilibrated with 15 bed volumes of 20 mM sodium acetate, pH 4.8 and packed into a column by using 20 mM acetate, pH 4.8 packing buffer. The supernatant from Step 1 was loaded onto the column at 3 mL/min flow rate and the column washed with 20 mM sodium acetate, pH 4.8 buffer. The flow-thorough and wash were combined. The $OD_{280}$ was measured against 20 mM sodium acetate, pH 4.8. The column was eluted with 50 mM sodium phosphate, 300 mM NaCl, pH 8.0 buffer and $OD_{280}$ of eluant as measured.

Step 3:

To 20 ml of Actigel ALD activated resin (Sterogene Bioseparations, Inc. Carlsbad, Calif.) the purified anti-*M. gallisepticum* chicken IgG solution was added at 10 mg/mL followed by 10.5 mL of 1M sodium cyanoborohydride (ALD Coupling Solution, Sterogene Bioseparations, Inc. Carlsbad, Calif.). The suspension was gently mixed for 20 hours at 2-8° C. followed by an extensive wash with DI water. The resin was stored in PBS, at pH 7.0 and 2-8° C.

Example 4

Purification of MG Antigens

Step 1:

To 20 mL of washed MG concentrate, 0.2 g Mega-10 detergent was added and mixed for 20 hours at room temperature. After 20 hours incubation, TRITON® X-100 nonionic surfactant detergent was also added to the suspension and mixing continued for another hour at room temperature. Subsequently, it was spun down at 5,000 rpm for 10 minutes. The supernatant was separated from the pellet and 200 mL of PBS, pH 7.2 was added to the supernatant. The MG protein solution was kept at 2-8° C. for 5 days.

Step 2:

A 20 mL bed volume anti-MG-chicken IgG-Actigel column was equilibrated with 5 bed volumes of PBS, pH 7.2 at 3 mL/min flow rate. The MG-protein solution was loaded onto the column at 8-15 mL/min. The flow-through was collected into the separate bottle. The column was washed with 10 bed volumes of PBS, pH 7.2 at 8-15 mL/min flow rate and then eluted with 20-40 mL of 0.1M citric acid, pH 2.5 at the same flow rate. The pH of the eluate was immediately adjusted to 7.2 by using 2 M Tris. This purification was repeated at least 5 times using the column flow-through in order to adsorb out all antigens. All eluates were combined and concentrated in a dialysis bag with powdered sugar overnight at 2-8° C. The concentrated solution was dialyzed against 5 L of PBS, pH 7.2 at 2-8° C. overnight. Bradford's protein assay was performed to determine concentration of purified antigen using serum albumin as standard.

Example 5

Activated Agarose Microparticles

Particles were activated by two different methods. The first activation method was performed by Sterogene Bioseparations, Inc. (Carlsbad, Calif.), using a commercially available proprietary aldehyde linkage chemistry, which provides for an extremely stable attachment of ligands. Another advantage of this chemistry is the high reproducibility of immobilization. This proprietary aldehyde chemistry allows consecutive immobilization of various ligands.

Another activation was performed by using a cyanogen bromide (CNBr) activation method. Briefly, to 30 mL of agarose microparticles 30 mL of 2 M sodium carbonate solution was added and kept in an ice bath for 3-5 minutes without mixing. Then, 1.5 g CNBr was weighed and dissolved into 9 mL acetonitrile. Immediately, the CNBr solution was added to the resin mixture and vigorously mixed on an ice bath for 2 minutes. Subsequently, it was washed with 20 bed volumes of ice cold water by spinning down at 4,500 rpm, 2° C. for 5 minutes.

Example 6

Coupling of MG Antigens to Microparticles

The coupling reaction takes place between amino groups on the purified antigens and the aldehyde groups or the CNBr-activated groups on the microparticles. When the aldehyde activated particles were used, the coupling was mediated with the coupling reagent sodium cyanoborohydride as described under Example 3. The antigens were immobilized at the concentrations of 10 µg/0.2 mL and 50 µg/0.2 mL microparticles.

In another coupling reaction the CNBr-activated microparticles were used at the same antigen concentration as follows. To 15 mL of CNBr activated microparticles, the purified MG antigen solution was added at pH 8.0. The solution was gently mixed at 2-8° C. for 20 h. The supernatant was separated by centrifugation and the resin washed with 10 bed volumes of DI water.

The coupled resins were stored in LAL water at 2-8° C. Bradford's protein assay was used to measure unbound protein in supernatant.

Example 7

Preparation and Coupling of *Mycoplasma* Membrane

To 3.0 mL of concentrated *mycoplasma* antigen 80 mL of autoclaved DI water was added and mixed with a stirring bar at 37° C. for 1 h. The solution was centrifuged at 5000 rpm for 30 min and the pellet washed twice with autoclaved water. The pellet was reconstituted in 10 mL of PBS. To 1.5 mL of CNBr activated microparticles, 0.5 mL of the purified pellet, diluted to 1:3 with 0.1 M $NaHCO_3$ at pH 8 was added. The solution was gently mixed at 2-8° C. for 20 h. The supernatant was separated by centrifugation and the resin washed with 10 bed volumes of DI water. The coupled resins were stored in LAL water at 2-8° C. Bradford's protein assay was used to measure unbound protein in supernatant.

Example 8

Coupling of NOD1 Receptor Activator to Microparticles

Peptidoglycan (PG), at 2 µg/0.2 mL resin, was dissolved in 0.1 M $NaHCO_3$ and added to CNBr-activated microparticles prepared according to Example 6. The reaction was allowed to run overnight at 2-8° C. The supernatant was separated by centrifugation and resin washed thoroughly with LAL grade water which is also the storage medium.

Example 9

Coupling of TLR3 Activator to Microparticles

Poly I:C at 10 µg/0.2 mL beads was immobilized to CNBr-activated microparticles in 0.1 M $NaHCO_3$ at pH 8, according to Example 6. The reaction was allowed to run overnight at 2-8° C. The supernatant was separated by centrifugation and resin washed thoroughly with LAL grade water which is also the storage medium.

Example 10

Coupling of TLR4 Activator to Microparticles

Bacterial lipopolysaccharide at 2 µg/0.2 mL resin was dissolved in 0.1 M $NaHCO_3$ at pH 8 and immobilized to CNBr-activated microparticles according to Example 6. The reaction was allowed to run overnight at 2-8° C. The supernatant was separated by centrifugation and resin washed thoroughly with LAL grade water which is also the storage medium.

Example 11

Coupling of TLR5 Activator to Microparticles

Flagellin at 2 µg/0.2 mL resin was dissolved in 0.1 M $NaHCO_3$ at pH 8 and immobilized to CNBr-activated microparticles according to Example 6. The reaction was allowed to run overnight at 2-8° C. The supernatant was separated by centrifugation and resin washed thoroughly with LAL grade water which is also the storage medium.

Example 12

Coupling of TLR1 and TLR6 Activator to Microparticles

Mycoplasmal MALP-2 containing surface antigen at 2 µg/0.2 mL resin was dissolved in 0.1M NaHCO$_3$ at pH 8 and immobilized to CNBr-activated microparticles according to Example 6. The reaction was allowed to run overnight at 2-8° C. The supernatant was separated by centrifugation and resin washed thoroughly with LAL grade water which is also the storage medium.

Example 13

Coupling of TLR7/TLR8 Activator to Microparticles

Single stranded RNA or antiviral imidazoquinolin Imiquimod (Aldara) at 2 µg/0.2 mL resin was dissolved in 0.1 M NaHCO$_3$ at pH 8 and immobilized to CNBr-activated microparticles according to Example 6. The reaction was allowed to run overnight at 2-8° C. The supernatant was separated by centrifugation and resin washed thoroughly with LAL grade water which is also the storage medium.

Example 14

Coupling of TLR9 Activator to Microparticles

The CpG DNA at 10 mL resin was dissolved in 0.1M NaHCO$_3$ at pH 8 and immobilized to CNBr-activated microparticles according to Example 6. The reaction was allowed to run overnight at 2-8° C. The supernatant was separated by centrifugation and resin washed thoroughly with LAL grade water which is also the storage medium.

Example 15

Immobilization of Combinational PAMP Recognition Receptor Agonist Molecule Compositions to Microparticles NOD1 agonist and TLR agonists 4 and 9 were mixed together at 2 µg/0.2 m: resin, 10 µg/0.2 mL resin and 2 µg/0.2 mL resin, respectively in 0.1 M NaHCO$_3$ at pH 8 and immobilized to CNBr-activated microparticles according to Example 6. The reaction was allowed to run overnight at 2-8° C. The supernatant was separated by centrifugation and resin washed thoroughly with LAL grade water and were stored in the same at 2-8° C.

Example 16

Immobilization of MG Antigen Along with Combinational PAMP Recognition Receptor Agonist Molecule Compositions to Microparticles MG antigens were coupled under conditions described in Example 6 for 1 h. Subsequently, the TLR agonist mixture described under Example 13 were added and the reaction was allowed to proceed overnight at 2-8° C. The supernatant was separated by centrifugation and resin washed thoroughly with LAL grade water which is also the storage medium.

Example 17

Animal Studies I

The results are the average of 3 experiments.
Three-days-old chicks (free of *M. gallisepticum* (MG) and *M. synoviae* (MS), and no MG and MS maternal antibodies to be detected by ELISA) were vaccinated. In each group there were 10 chickens. At 14 days of the experiment, chickens were challenged with *M. gallisepticum* R$_{low}$ strain. The study was terminated at 28 days.

The groups were set up as follows:
G1-G5 Treatment with Microparticle Vaccine Compositions Prior to Challenge
    G1=treated orally with microparticles (0.2 mL/chicken) only and challenged
    G2=treated orally with microparticles (0.2 mL/chicken) with *M. gallisepticum* affinity purified antigen (10 µg/dose) and challenged
    G3=treated orally with microparticles (0.2 mL/chicken) with receptor agonists (10 µg bacterial DNA, *E. coli*+2 µg *E. coli* LPS and 2 µg peptidoglycan/dose) and challenged
    G4=treated orally with microparticles (0.2 mL/chicken) with *M. gallisepticum* affinity purified antigen (10 µg/dose) and receptor agonists (10 µg bacterial DNA, *E. coli*+2 µg *E. coli* LPS and 2 µg peptidoglycan/dose) and challenged
    G5=treated orally with microparticles (0.2 mL/chicken) with *M. gallisepticum* membrane ($10^7$/dose)
G6-G7 Treatment with Microparticle Vaccine Compositions Post-Challenge
    G6=challenged and treated orally post-challenge with microparticles (0.2 mL/chicken) with *M. gallisepticum* affinity purified antigen (10 µg/dose) and receptor agonists (10 µg bacterial DNA, *E. coli*+2 µg *E. coli* LPS and 2 µg peptidoglycan/dose)
    G7=challenged and treated orally post-challenge with microparticles (0.2 mL/chicken) with receptor agonists (10 µg bacterial DNA, *E. coli*+2 µg *E. coli* LPS and 2 µg peptidoglycan/dose)
G8 and G9 Positive and Negative Controls
    G8=challenged and non-treated
    G9=non-challenged and non-treated
Timeline
    Day-1: Setting-up of groups G1-G9. Sacrificed 10 chickens for ELISA assay, PCR and culturing of *M. gallisepticum* and *M. synoviae* to confirm that the experimental chickens are negative for maternal antibodies and the presence of *M. gallisepticum* and *M. synoviae*.
    Day 0: Vaccination of G1-G5 prior to challenge.
    Day 14: Challenge of groups G1-G8.
    Day 15: Vaccination of groups G6-G7 post-challenge.
    Day 28: G1-G9. Euthanasia, necropsy, and plating for the isolation of *M. gallisepticum* (MG) from specified organs, trachea, air sac and lung. Histological examinations of trachea and lung were performed.
    Days D14 and D28: Chickens were bled in order to obtain serum to be tested for MG-specific antibodies using a serum plate agglutination (SPA) test and blocking ELISA.

On D-1 a total of 90, one-day-old broiler breeder chickens were allocated to one of eight groups (10 birds/group). The chicken's individual body weights were recorded. The chickens were allocated such that their average body weight in each group would not be markedly different. Each bird were identified by coloured and numbered wing tags according to the treatment and their body weight recorded on the appropriate form.

Treatment

On Day 0, chickens of G1-G5 were treated with different composition of the vaccine, 0.2 mL in 1 mL PBS per animal. Doses are described above. G6-G7 was treated on day 15, post-challenge.

Challenge

At day D14, eight groups of animals G1-G8 were challenged using a fresh broth culture of the virulent R-strain of *M. gallisepticum*, at a titre of about 8.0 $\log_{10}$ CFU/ml. Ten ml of this fresh broth culture was administered to each of these groups using a spray technique. Briefly, the birds were placed in a 0.22 cubic meter isolation unit. Ten ml of fresh *M. gallisepticum* R-strain culture was then sprayed, under a pressure of 1 atmosphere, for about a 100 second duration and the chickens left exposed for 20 minutes. (In the laboratory, successful results have been obtained in several experiments using this technique).

Euthanasia and Pathology

On D28, at the end of the experimental study, all groups were euthanized. Each bird is necropsied and scored for gross lesions associated with MG. Presence of exudate in the trachea, left and right thoracic air sacs and peritoneum were recorded. The lesions are scored according to the following system:

In trachea: 0=no exudates, 1=slight redness and small quantity of exudates, 2=redness of mucous membrane, exudates. Left and right air sacs: 0=no lesion, 1=serous exudates, 2=serous exudates with small pieces of fibrin, 3=serous, fibrinous exudates, slightly thickened air sac wall, 4=lots of fibrinous exudates, very thickened air sac wall.
Peritoneum: 0=no exudates, 1=serous exudates, 2=serous exudate with small pieces of fibrin, 3=serous-fibrinous exudates.

MG Isolation

During necropsy examination, trachea, thoracic air sacs, liver, lung, spleen, kidney and heart were aseptically sampled using swabs. Materials from the swabs were then plated onto *mycoplasma* agar (MA) and incubated at 37° C. in a 5% $CO_2$ incubator. Plates were observed for *mycoplasma* on days 2, 4, and 7, and then at weekly intervals for a maximum of three weeks. Positive colonies were tested by PCR to identify *M. gallisepticum* and *M. synoviae*.

Necropsy

Subsequent to MG challenge, significant pathological lesions were recognized in the air-sac and the peritoneum. However, significant reduction in lesion scores was recorded in the groups treated with particles plus receptor agonists (G3, G6 p<0.001), particles plus purified antigen (G2, p<0.001) and purified antigen plus receptor agonists (G4, G6 p<0.001) in comparison with the control (G8) non-treated, challenged group as well as the group treated with particles only (G1). However, better results were obtained with particles plus purified antigen or particles plus purified antigen plus receptor agonists if they were administered before challenge when compared to administration after challenge. When G5 was treated with *M. gallisepticum* membrane immobilized to the particles the pathological lesions in some cases were more pronounced than in the challenge group itself. This leads to the conclusion that the vaccination with the *M. gallisepticum* membrane prevented the appropriate immune response against the challenge with the pathogen, causing immune suppression and allowing a more pronounced infection.

Re-Isolation of *Mycoplasma*

*Mycoplasma* can be re-isolated frequently from the inner organs of the non-vaccinated, infected control chickens. Significant reduction in re-isolation rate (from respiratory+inner organs) was noticed in groups treated with particles plus purified antigen with or without receptor agonists (G2, G4, G6) in comparison to the non-vaccinated control (G8, p<0.01) group and to the group treated with particles only (G1, p<0.001-0.01) or treated with particle plus receptor agonists (G3, G7 p<0.05). However, there was significantly lower re-isolation rate (p<0.05) between the group treated with particles plus receptor agonists (G3, G6) and the control (G8). Similar results were obtained when the re-isolation rate of *mycoplasma* from respiratory track (trachea, lung, air-sac) or from other inner organs (liver, spleen, kidney and heart) of the experimental groups were compared. When G5 was treated with *M. gallisepticum* membrane immobilized to the particles the reisolation rate of *M. gallisepticum* from the organs in some cases was higher than in the challenge group itself. This leads to the conclusion that the vaccination with the *M. gallisepticum* membrane prevented the appropriate immune response against the challenge with the pathogen and causing immune suppression and allowing a more pronounced infection.

The results are shown in Table 1.

TABLE 1

| Groups | Percentage of lesion scores Necropsy results | Vaccine efficiency | Percentage of *M. gallisepticum* reisolation from inner organs | Vaccine efficiency |
| --- | --- | --- | --- | --- |
| G1 - particles only | 86.0% | 14% | 70.8% | 29.2% |
| G2 - particles + 10 µg antigen | 47.8% | 53.2% | 34.6% | 65.4% |
| G3 - particles + PRR agonists | 71.3% | 28.7% | 56.4% | 43.6% |
| G4 - particles + 10 µg antigen + PRR agonists | 25.5% | 74.5% | 12.7% | 87.3% |
| G5 - panicles + *M. gallisepticum* membrane | 99.4% | 0.6% | 96.1% | 3.9% |
| G6 - post challenge: particles + 10 µg antigen + PRR agonists | 38.0% | 62% | 16.7% | 83.3% |
| G7 - post challenge: particles + PRR agonists | 74.0% | 26% | 58.3% | 41.7% |
| G8 - challenged control | 100% | 0 | 100% | 0 |
| G9 - non-challenged control | 0 | 0 | 0 | 0 |

Serological Results

Serological response of the groups was different at the end of the experiment. The reaction of the non-treated, challenged group (G8) did not differ from the group treated with particles only (G1). At the same time, significantly stronger reaction was noticed in the group treated with particles plus purified antigen and PRR agonists (G4) ($p<0.05$) over the group treated with particles (G1) only. Compared to the group treated with particles plus purified antigen (G2), if PRR was added (G4, G6) a significantly higher serological response was noted ($p<0.05$). There was no significant difference between the serological results if the particles with antigen and PRR were used prior (G4) or after (G6) the challenge.

Discussion

*M. gallisepticum* can cause significant inflammation in the air-sac and peritoneum which is accompanied by colonization of trachea, air-sac and the lungs. *Mycoplasma* can also be detected frequently from inner organs. We have developed a new type of "pathogen mimicking" immunologically active compositions consisting of microparticles in the size range of microorganisms (<5 µm), having immunoaffinity purified antigens covalently immobilized along with different PRR agonist molecules.

Our results showed that the particles without any modification did not stimulate any immune response. The particles alone did not protect the chickens from peritonitis and air-sacculitis caused by *M. gallisepticum* nor did it prevent the colonization of organs by *mycoplasma*.

When the particles were coated with PRR agonist without antigen, serological response to *mycoplasma* challenge was not affected. However, colonization of organs with *mycoplasma* was reduced and the scores of pathological lesions were reduced. This confirms our in vitro observations that PRR agonists do stimulate or enhance the innate immune response leading to increased protection. However, the amount of immune modulator applied was not able to fully protect the animal from a massive dose of challenge with a highly pathogenic strain. This is also known for the innate immune system as it is typically insufficient to overcome massive doses of pathogens. However, the data indicates, that this novel immune modulator could possibly protect the animal from a lower dose of challenge.

When purified antigen was added to the particles coated with PRR agonists, *mycoplasma* specific serological response was enhanced. The colonization of organs was reduced significantly and scores of pathological lesions was low. This effect was more pronounced when the vaccine was introduced mucosally and before challenge, but similar positive effect was noticed when the vaccine was administered mucosally after the challenge.

An interesting observation was that increasing antigen concentrations (up to 50 µg/dose) actually decreased the protective effects of the vaccine. This suggested the presence of immunosuppressive components in the affinity-purified antigen. To identify such components and eliminate their effects a new animal trial was designed (see below).

After vaccination, prior to challenge the vaccinated chickens were examined daily to evaluate the safety of the vaccine. The chickens were found to be clinically healthy, showed no side effects from the vaccine. The feed and water consumption of the birds did not change as compared to the non-vaccinated groups. The animals necropsied during the course of the trial showed no signs of inflammation or change in organ size/weight. The vaccine appears to be safe.

Example 18

Affinity purified MG antigen was prepared as described in the previous Examples. The purified antigen was divided into three groups for the following treatments prior to immobilization.

1. Endoglycosidase H Digestion

To 53.6 ml of antigens (about 1.5 mg) 2.5 Units of enzyme was added and incubated at 37° C. overnight. The next day the mixture was passed through a chilled immobilized Mannan column (5 mL) and the flow through was collected. This sample was designated Endo H Antigens.

2. Periodate Treatment

To 53.6 mL of antigens (about 1.5 mg) solid sodium periodate was added to a final concentration of 15 mM and after mixing kept chilled for 1 hour. Glycerin in a two-fold molar access was added and the sample incubated for another hour. Dialysis against PBS was performed overnight. The dialyzed sample is designated Periodate (PJ) Antigens.

3. Removal of ConA Binding Antigens

Purified antigens (about 1.5 mg in 53.6 mL) were passed through a 2 mL immobilized Con A column. The flow-through was collected. This sample is designated Con A flowthrough. The bound antigens were eluted with 1M alpha-methyl mannoglucoside in 50 mM TRIS, pH 9.5. This sample is designated Con A elution.

Antigen Treatment

The characteristics of the antigens are shown in Table 2.

TABLE 2

|  | $OD_{280\,nm}$ | Protein (mg/ml) | Total protein (mg) (% recovery) |
| --- | --- | --- | --- |
| Initial antigens | 0.1005 | 0.0284 | 1.52* |
| Con A flowthrough | 0.0818 | 0.0179 | 1.00 (66) |
| Con A elution | 0.0045 | 0.0084 | 0.088 (5.7) |
| Endo H antigens | 0.0660 | 0.0210 | 1.81 (72) |
| Periodate antigens | 0.1110 | 0.0296 | 1.67 (100) |

*for Endo H treatment, the initial amount of antigens treated was 2.51 mg. (53.6 ml of this preparation and 40.3 ml of a previous *M. gallisepticum* preparation at 0.0246 mg/ml).

Example 19

Animal Studies II

The results are the average of 3 experiments. Three-days-old chicks (free of *M. gallisepticum* (MG) and *M. synoviae* (MS), and no MG and MS maternal antibodies to be detected by ELISA) were vaccinated. In each group there were 10 chickens. At 14 days of the experiment, chickens were challenged with *M. gallisepticum* $R_{low}$ strain. The study was terminated at 28 days.

The groups were set up as follows:
G1=non-challenged and non-treated
G2=challenged and non-treated
Treated 2 weeks prior challenge:
G3=treated orally with microparticles (0.2 mL/chicken) with *M. gallisepticum* affinity purified antigen (10 µg/dose) and TLR agonists (10 µg bacterial DNA, *E. coli*+2 µg *E. coli* LPS and 2 µg peptidoglycan/dose) and challenged
G4=treated orally with microparticles (0.2 mL/chicken) with *M. gallisepticum* affinity purified antigen (50 µg/dose) and TLR agonists (10 µg bacterial DNA, *E. coli*+2 µg *E. coli* LPS and 2 µg peptidoglycan/dose) and challenged
G5=treated orally with microparticles (0.2 mL/chicken) with *M. gallisepticum* affinity purified ConA adsorbed antigen (10 µg) and challenged G6=treated orally with microparticles (0.2 mL/chicken) with *M. gallisepticum* affinity purified Endo H digested antigen (10 µg) and challenged G7=treated orally with microparticles (0.2 mL/chicken) with *M. gallisepticum* affinity purified periodate oxidized antigen (10 µg) and challenged G8=treated orally with microparticles (0.2 mL/chicken) with *M. gallisepticum* affinity purified Con A adsorbed antigen (10 µg)+TLR agonists (10 µg bacterial DNA, *E. coli*+2 µg *E. coli* LPS and 2 µg peptidoglycan/dose) and challenged G9=treated orally with microparticles (0.2 mL/chicken) with *M. gallisepticum* affinity purified Con A adsorbed antigen (50 µg)+TLR agonists (10 µg bacterial DNA, *E. coli*+2 µg *E. coli* LPS and 2 µg peptidoglycan/dose) and challenged G10=treated orally with microparticles (0.2 mL/chicken) with *M. gallisepticum* affinity purified Endo H digested antigen (10 µg)+TLR agonists (10 µg bacterial DNA, *E. coli*+2 µg *E. coli* LPS and 2 µg peptidoglycan/dose) and challenged G11=treated orally with microparticles (0.2 mL/chicken) with *M. gallisepticum* affinity purified Endo H digested antigen (50 µg)+TLR agonists (10 µg bacterial DNA, *E. coli*+2 µg *E. coli* LPS and 2 µg peptidoglycan/dose) and challenged G12=treated orally with microparticles (0.2 mL/chicken) with *M. gallisepticum* affinity purified periodate oxidized antigen (10 µg)+TLR agonists (10 µg bacterial DNA, *E. coli*+2 µg *E. coli* LPS and 2 µg peptidoglycan/dose) and challenged G13=treated orally with microparticles (0.2 mL/chicken) with *M. gallisepticum* affinity purified periodate oxidized antigen (50 µg)+TLR agonists (10 µg bacterial DNA, *E. coli*+2 µg *E. coli* LPS and 2 µg peptidoglycan/dose) and challenged G14=treated orally with microparticles (0.2 mL/chicken) with *M. gallisepticum* affinity purified Endo H digested antigen (10 µg)+TLR agonists (10 µg bacterial DNA, *E. coli*+2 µg *E. coli* LPS and 2 µg peptidoglycan/dose) plus aminoguanidine (i.p.) for 7 days and challenged G15=treated orally with microparticles (0.2 mL/chicken) with *M. gallisepticum* antigen Con A eluate on beads and challenged Timeline Day-1: Setting-up of groups G1-G15. Sacrificed 10 chickens for ELISA assay, PCR and culturing of *M. gallisepticum* and *M. synoviae* to confirm that the experimental chickens are negative for maternal antibodies and the presence of the *mycoplasma*.

Day 0: Vaccination of G3-G14 prior to challenge.

Day 14: Challenge of groups G2-G15.

Day 28: G1-G15. Euthanasia, necropsy, and plating for the isolation of *M. gallisepticum* (MG) from specified organs, trachea, air sac and lung. Histological examinations of trachea and lung were performed.

Days D14 and D28: Chickens were bled in order to obtain serum to be tested for MG-specific antibodies using a serum plate agglutination (SPA) test and blocking ELISA.

On D-1 a total of 150, one-day-old broiler breeder chickens were allocated to one of 15 groups (10 birds/group). The chicken's individual body weights were recorded. The chickens were allocated such that their average body weight in each group would not be markedly different. Each bird were identified by coloured and numbered wing tags according to the treatment and their body weight recorded on the appropriate form.

Challenge

At day D14, fourteen groups of animals G2-G15 were challenged using a fresh broth culture of the virulent R-strain of *M. gallisepticum*, at a titre of about 8.0 $\log_{10}$ CFU/ml. Ten ml of this fresh broth culture was administered to each of these groups using a spray technique. Briefly, the birds were placed in a 0.22 cubic meter isolation unit. Ten ml of fresh *M. gallisepticum* R-strain culture was then sprayed, under a pressure of 1 atmosphere, for about a 100 second duration and the chickens left exposed for 20 minutes. (In the laboratory, successful results have been obtained in several experiments using this technique).

Euthanasia and Pathology

On D28, at the end of the experimental study, all groups were euthanized. Each bird is necropsied and scored for gross lesions associated with MG. Presence of exudate in the trachea, left and right thoracic air sacs and peritoneum were recorded. The lesions are scored according to the following system:

In trachea: 0=no exudates, 1=slight redness and small quantity of exudates, 2=redness of mucous membrane, exudates. Left and right air sacs: 0=no lesion, 1=serous exudates, 2=serous exudates with small pieces of fibrin, 3=serous, fibrinous exudates, slightly thickened air sac wall, 4=lots of fibrinous exudates, very thickened air sac wall.

Peritoneum: 0=no exudates, 1=serous exudates, 2=serous exudate with small pieces of fibrin, 3=serous-fibrinous exudates.

Results

The results are shown in Table 3.

TABLE 3

| Groups | Lesion Scores | Re-isolation | Efficiency |
|---|---|---|---|
| Non-treated, non-challenged | 0 | 0 | N/A |
| Non-treated, challenged | (92) 100% | 100% | 0% |
| G4: 50 µg A + TLR | (52) 56.5% | 66.6% | 33.4% |
| G9: Con A 50 µg A + TLR | (10) 10.9% | 83% | 91.7% |
| G11: EndoH 50 µg A + TLR | (17) 18.5% | 0% | 100% |
| G13: PJ 50 µg A + TLR | (21) 22.8% | 16.7% | 83.3% |
| G15: Con A eluted A | (53) 57.6% | 100% | 0% |

MG Isolation

During necropsy examination, trachea, thoracic air sacs, liver, lung, spleen, kidney and heart were aseptically sampled using swabs. Materials from the swabs were then plated onto *mycoplasma* agar (MA) and incubated at 37° C. in a 5% $CO_2$ incubator. Plates were observed for *mycoplasma* on days 2, 4, and 7, and then at weekly intervals for a maximum of three weeks. Positive colonies were tested by PCR to identify *M. gallisepticum* and *M. synoviae*.

Necropsy and Re-Isolation

Subsequent to MG challenge, significant pathological lesions were recognized in the air-sac and the peritoneum. However, significant reduction in lesion scores and re-isolation rates were recorded in the groups vaccinated with treated purified antigen plus TLR groups, the best of which was the Con A column depleted antigen (G9) in comparison with the control non-treated, challenged group. However, with the Con A-eluted antigen fraction G15 the pathogen lesion score was high and the re-isolation rate was the same as with the positive control. This leads to the conclusion that the vaccination with this *M. gallisepticum* antigen fraction prevented the appropriate immune response against the challenge with the pathogen, causing immune suppression and allowing a more pronounced infection.

Discussion

The results of these experiments showed that the removal of immune suppressive antigens from the affinity purified antigen pool has markedly improved the protective effects of the vaccine composition. In addition, the chemical modification or enzymatic breakdown of the sugar containing post-transcriptional modifications on the antigens also led to an improved protective immunity.

Conversely, we have also found that the administration of the isolated immune suppressive antigens coupled to microparticles lead to immune suppression and the development of tolerance to the pathogen. This way we have demonstrated that proper antigen characteristics can shift the immune response towards either protection or tolerance. Both of these have a great significance in developing rational approaches to modulating immune responses. Subsequently, we have decided to target additional antigenic surface determinants involved in the development of immune responses.

Example 20

Affinity purified MG antigen was prepared as described in the previous Examples. The purified antigen was divided into three groups for the following treatments prior to immobilization.
1. MG Antigen Deacylation To 27 mL of antigens (about 0.65 mg) 8 mL of 1 M NaOH and 10 mg of pentadecanoic acid were added and the solution was gently agitated at 70° C. for 45 min. The pH was then adjusted to 8.0 and the precipitate removed by centrifugation at 3,000 rpm for 5 min. This sample was designated Deacylated Antigens.
2. Periodate Treatment This was intended to be a more stringent reaction than that of Example 18. To 25 mL of antigens (about 0.6 mg) solid sodium periodate was added to a final concentration of 80 mM and after mixing kept for 2.5 hours at room temperature. Glycerin in a two-fold molar access was then added and the sample incubated for another hour. Dialysis against PBS was performed overnight. The dialyzed sample is designated Periodate Antigens.

Example 21

Animal Studies III

The results are the average of 3 experiments. Three-days-old chicks (free of *M. gallisepticum* (MG) and *M. synoviae* (MS), and no MG and MS maternal antibodies to be detected by ELISA) were vaccinated. In each group there were 10 chickens. At 14 days of the experiment, chickens were challenged with *M. gallisepticum* $R_{low}$ strain. The study was terminated at 28 days.

The groups were set up as follows:
G1=non-challenged and non-treated
G2=challenged and non-treated
Treated 2 weeks prior challenge:
G3=treated orally with microparticles (0.2 mL/chicken) with *M. gallisepticum* affinity purified, Con A adsorbed antigen (10 µg/dose)+TLR agonists (10 µg bacterial DNA, *E. coli*+2 µg *E. coli* LPS and 2 µg peptidoglycan/dose) and challenged
G4=treated orally with microparticles (0.2 mL/chicken) with *M. gallisepticum* affinity purified, deacylated antigen (10 µg/dose)+TLR agonists (10 µg bacterial DNA, *E. coli*+2 µg *E. coli* LPS and 2 µg peptidoglycan/dose) and challenged
G5=treated orally with microparticles (0.2 mL/chicken) with *M. gallisepticum* affinity purified, ConA adsorbed antigen (10 µg)+TLR agonists (25 µg poly I:C+10 µg bacterial DNA and 2 µg peptidoglycan/dose) and challenged G6=treated orally with microparticles (0.2 mL/chicken) with *M. gallisepticum* affinity purified periodate treated and deacylated antigen (10 µg)+TLR agonists (10 µg poly I:C+10 µg bacterial DNA, and 2 µg peptidoglycan/dose) and challenged
Treated 1 day after challenge:
G7=treated orally with microparticles (0.2 mL/chicken) with *M. gallisepticum* affinity purified Con A adsorbed antigen (10 µg)+TLR agonists (25 µg poly I:C+10 µg bacterial DNA, and 2 µg peptidoglycan/dose)
G8=treated orally with microparticles (0.2 mL/chicken) with *M. gallisepticum* affinity purified periodate treated and deacylated antigen (10 µg)+TLR agonists (25 µg poly I:C+10 µg bacterial DNA, and 2 µg peptidoglycan/dose) and challenged
Timeline Day-1: Setting-up of groups G1-G9. Sacrificed 10 chickens for ELISA assay, PCR and culturing of *M. gallisepticum* and *M. synoviae* to confirm that the experimental chickens are negative for maternal antibodies and the presence of the mycoplasma.

Day 0: Vaccination of G3-G6 prior to challenge.
Day 14: Challenge of groups G2-G9.
Day 15: Vaccination of G7-G9 subsequent to challenge.
Day 28: G1-G9. Euthanasia, necropsy, and plating for the isolation of *M. gallisepticum* (MG) from specified organs, trachea, air sac and lung. Histological examinations of trachea and lung were performed.

Days D14 and D28: Chickens were bled in order to obtain serum to be tested for MG-specific antibodies using a serum plate agglutination (SPA) test and blocking ELISA.

On D-1 a total of 90, one-day-old broiler breeder chickens were allocated to one of 9 groups (10 birds/group). The chicken's individual body weights were recorded. The chickens were allocated such that their average body weight in each group would not be markedly different. Each bird were identified by coloured and numbered wing tags according to the treatment and their body weight recorded on the appropriate form.
Challenge At day D14, nine groups of animals G2-G9 were challenged using a fresh broth culture of the virulent R-strain of *M. gallisepticum*, at a titre of about 8.0 $\log_{10}$ CFU/ml. Ten ml of this fresh broth culture was administered to each of these groups using a spray technique. Briefly, the birds were placed in a 0.22 cubic meter isolation unit. Ten ml of fresh *M. gallisepticum* R-strain culture was then sprayed, under a pressure of 1 atmosphere, for about a 100 second duration and the chickens left exposed for 20 minutes.
Euthanasia and Pathology On D28, at the end of the experimental study, all groups were euthanized. Each bird is necropsied and scored for gross lesions associated with MG. Presence of exudate in the trachea, left and right thoracic air sacs and peritoneum were recorded. The lesions are scored according to the following system:
In trachea: 0=no exudates, 1=slight redness and small quantity of exudates, 2=redness of mucous membrane, exudates. Left and right air sacs: 0=no lesion, 1=serous exudates, 2=serous exudates with small pieces of fibrin, 3=serous, fibrinous exudates, slightly thickened air sac wall, 4=lots of fibrinous exudates, very thickened air sac wall.
Peritoneum: 0=no exudates, 1=serous exudates, 2=serous exudate with small pieces of fibrin, 3=serous-fibrinous exudates.

Results

The results are shown in Table 4.

TABLE 4

| Groups<br>All 10 µg antigen | Necropsy<br>score | Effi-<br>ciency | Re-<br>isolation<br>score | Effi-<br>ciency |
|---|---|---|---|---|
| G1 Control− | 0 | 100% | 0 | 100% |
| G2 Control+ | 78 | 0% | 23 | 0% |
| G3 ConA + TLR 2, 4, 9 | 19 | 76% | 5 | 79% |
| G4 Deacylated + TLR 2, 4, 9 | 19 | 76% | 2 | 92% |
| G5 ConA + TLR 3, 4, 9 | 18 | 77% | 3 | 87% |
| G6 Periodate treated and deacylated + TLR 3, 4, 9 | 21 | 74% | 4 | 83% |
| G7 ConA + TLR 3, 4, 9 | 26 | 67% | 0 | 100% |
| G8 Periodate treated and deacylated + TLR 3, 4, 9 | 19 | 76% | 6 | 74% |

MG Isolation

During necropsy examination, trachea, thoracic air sacs, liver, lung, spleen, kidney and heart were aseptically sampled using swabs. Materials from the swabs were then plated onto *mycoplasma* agar (MA) and incubated at 37° C. in a 5% $CO_2$ incubator. Plates were observed for *mycoplasma* on days 2, 4, and 7, and then at weekly intervals for a maximum of three weeks. Positive colonies were tested by PCR to identify *M. gallisepticum* and *M. synoviae*.

Necropsy and Re-Isolation

Subsequent to MG challenge, significant pathological lesions were recognized in the air-sac and the peritoneum. However, significant reduction in lesion scores and re-isolation rates were recorded in the groups vaccinated with treated purified antigen plus TLR groups, all groups gave comparable results, the deacylated antigen (G4) were the best in comparison with the control non-treated, challenged group. In the post-infection vaccinated groups, the Con A treated antigen plus TLR 3, 4, 9 gave the best results. It appears that it is possible to achieve a protective immunity even post-infection with this composition.

Discussion

The results of these experiments showed that the removal or blocking of immune suppressive escape antigens or antigenic determinants from the affinity purified antigen pool has markedly improved the protective effects of the vaccine composition. In addition, the removal of and the chemical modification of the sugar containing post-transcriptional modifications (N-glycosylation) on the antigens also led to an improved protective immunity. In addition, lipid moieties on antigens were chemically removed or blocked that also led to marked immune protective effects.

We have again demonstrated that with proper antigen modifications it is possible to shift the immune response towards protection. This has a great significance in developing rational approaches to modulating immune responses. Subsequently, we have set up an in vitro system to reproduce the respective immune responses in tissue culture. Such system may have a predictive value as to immune response produced by the immunologically active composition and thus can shorten the product development cycle.

Example 22

In Vitro Studies

TNF-α secretion was measured in PBMC prepared from peripheral blood and treated with peptidoglycan (PepG) (Sigma, St Louis, Mo., bacterial CpG DNA (KM Biomedicals, Aurora, Ohio; LPS<0.2 EU/ml measured by the *Limulus amoebocyte lysate* assay), or both. TNF-α was measured by ELISA from the culture supernatant after 5 hours incubation.

Tissue Factor (TF) in monocytes, representative of the innate immune system, was extracted from the corresponding PBMC cultures used for TNF-α analysis. TF was extracted from the adherent cells with TRITON® X-100 nonionic surfactant detergent as recommended by the manufacturer for TF ELISA (Imubind kit, American Diagnostica, Greenwich, Conn.).

Figure 2A:
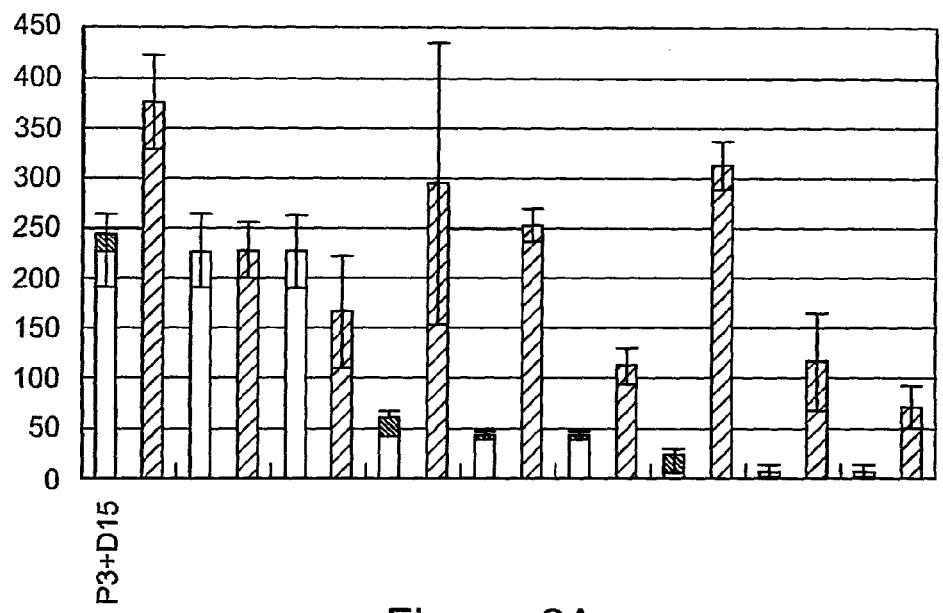
FIG. 2 is a graph showing the secretion of TNF-α by PBMC (A) or secretion of Tissue Factor (B) after treatment with peptidoglycan (PepG) (white bar), or bacterial CpG DNA (bactDNA) (black bar), or both simultaneously at the same concentration as when added alone (hatched bar); the numbers following P and D, respectively, indicate the concentrations of PepG and bactDNA in µg/ml respectively; left to right, they are P3+D15, P3+D5, P3+D1.5, P1+D15, P1+D5, P1+D1.5, P0.3+D15, P0.3+D5, and P0.3+D1.5.
Figure 2B:
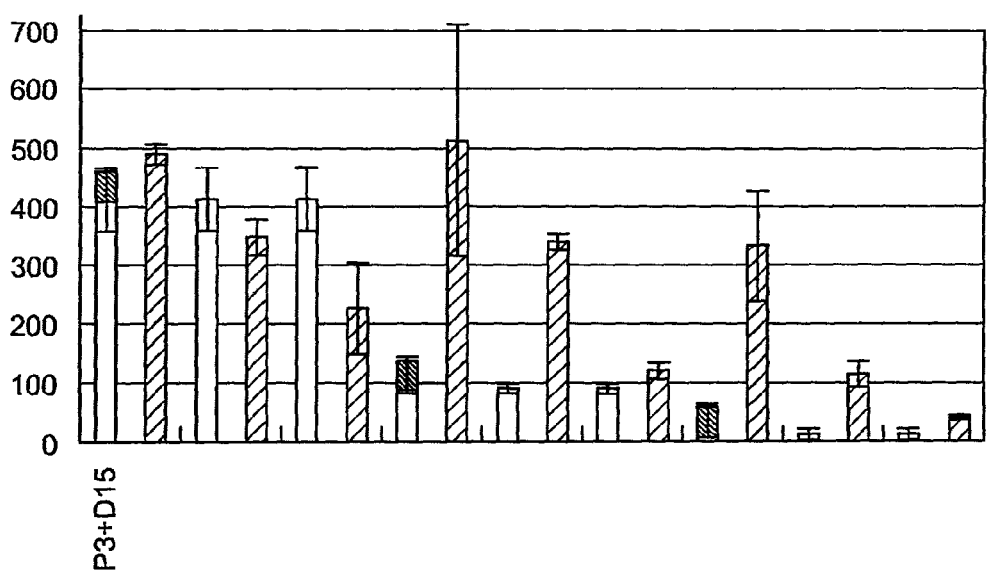

The results are shown in FIG. 2 (the numbers following P and D, respectively, indicate the concentrations of PepG and bactDNA in µg/ml respectively; left to right, they are P3+D15, P3+D5, P3+D1.5, P1+D15, P1+D5, P1+D1.5, P0.3+D15, P0.3+D5, and P0.3+D1.5). TNF-α secreted by PBMC (A) and Tissue Factor (B) after treatment with PepG (white bar), or bacterial CpG DNA (black bar), or both simultaneously at the same concentration as when added alone (hatched bar). The numbers following P and D, respectively, indicates the concentrations of PepG and bactDNA in µg/mL respectively. $P<0.05$ for TNF-α and TF, when comparisons were made between the sum of the effects of PepG (3 or 1.5 µg/mL) and CpG DNA alone at all concentrations tested, and when PepG and bactDNA were added together; Student's t-test (n=4). This is a representative experiment out of three.

The present results demonstrate the concomitant induction of TNF-α and TF by PepG and bactDNA in PBMC, and a synergistic effect between the two molecules. This could involve direct effects on common downstream signaling pathways, or indirect effects mediated by secreted compounds following PepG or bactDNA action. TNF-α is an important early mediator of host responses to pyrogens and is the only endogenous mediator capable of triggering the entire spectrum of metabolic, hemodynamic, tissue and cytokine cascade responses of septic shock. The synergistic effects of bactDNA and PepG have implications for the pathogenesis of sepsis, where each molecule, although present at low concentrations in vivo, is likely to amplify the effect of another one, as hypothesized previously.

Demonstration of in vitro Induction of Different Th1 and Th2 Responses by Different Particle Compositions Peripheral blood mononuclear cells were prepared by Ficoll separation of peripheral blood from healthy volunteers. Mononuclear cells were plated at a density of $10^6$ cells/ml in 1.5 ml RPMI-1640 (Irvine Scientific, Irvine, Calif.), supplemented with 100 U/ml Penicillin/Streptomycin, 2 mM Glutamine and 3% fetal calf serum, and incubated with 0.15 mL of microparticles (in sterile PBS) for 18 h. The microparticles contained Con A-stripped or sodium periodate treated antigens as well as TLR agonists 2, 3, 4 and 9 as indicated in the graph below. The preparation of the beads is described in Example 19.

Figure 3:
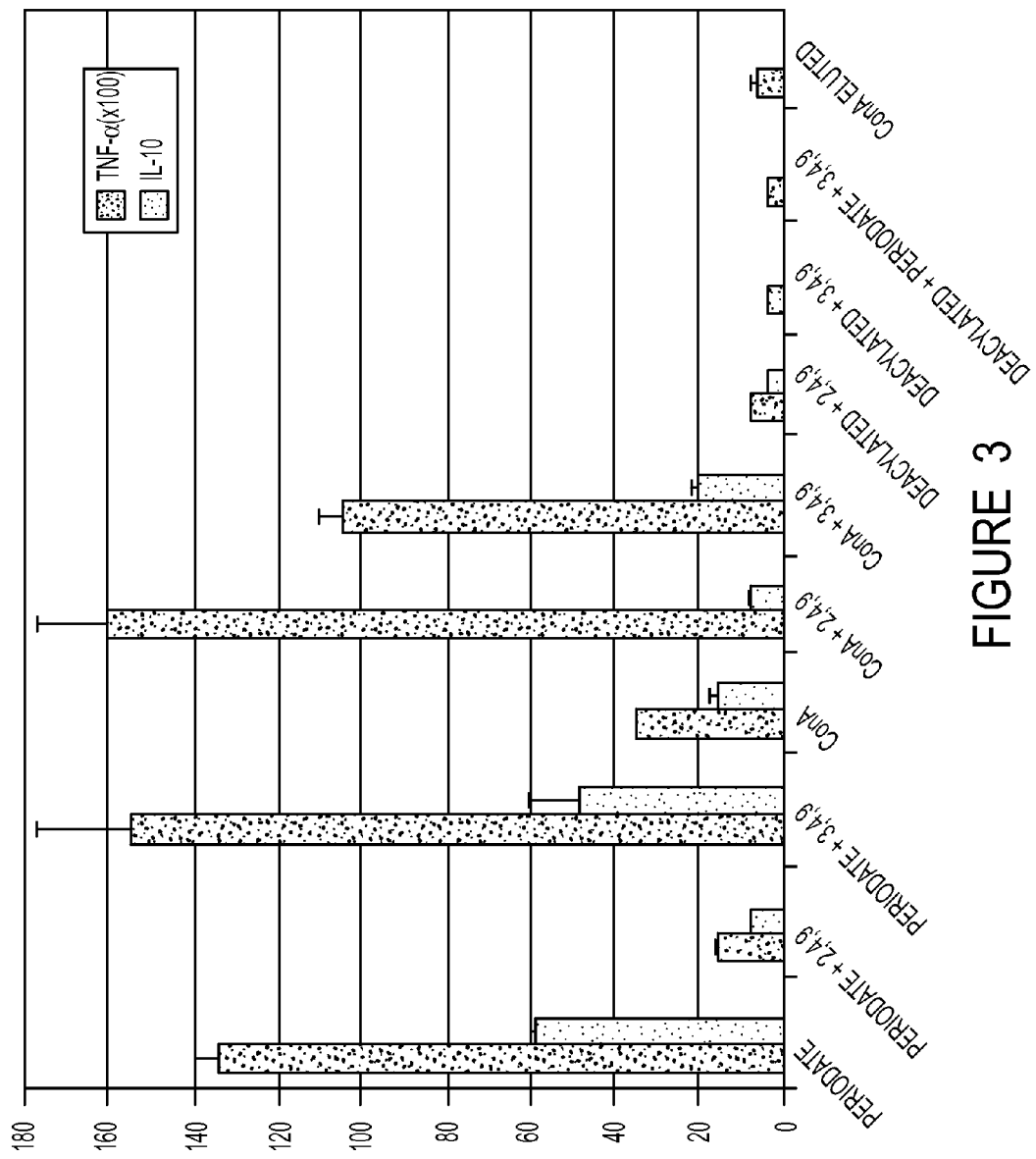
FIG. 3 is a graph showing the induction of different Th1 and Th2 responses by particles prepared in different ways with Con A-stripped or sodium periodate treated antigens as well as various combinations of TLR2, TLR3, TLR4, and TLR9 agonists (grey bar, TNF-α×100, black bar, IL-10)
Figure 4:
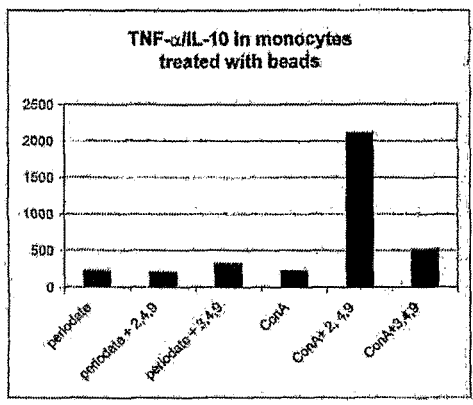
FIG. 4 is a graph showing the TNF-α/IL-10 ratio for monocytes treated with particles prepared in different ways as for FIG. 3.

The results are shown in FIG. 3 (grey bar, TNF-α×100, black bar, IL-10) and in FIG. 4, where the ratios of TNF-α/IL-10 are shown.

The TNF-α and IL-10 ratio analysis demonstrated that the Con A-depleted antigen co-immobilized with TLR 2, 4, 9 gave the most marked Th1 response that was found to correlate with in vivo results (see Example 19). This composition gave consistently the highest protective effect to mycoplasmal challenge in animals.

Example 23

To further characterize the cellular response to the immunomodulator microparticle, we exposed dendritic cells to such microparticles. We have observed an up-regulation of the MHC I and MHC II molecules and the co-stimulatory molecule CD80 and CD86. The presence of either PRR agonist combinations seems necessary to measure an MHC II increase on the surface of dendritic cells after 18 hours of treatment. Since the MHC presence at the cells surface is a dynamic process, a different incubation time with ConA Ag beads may be needed to observe an increase in MHC molecules at the cell surface. MHC allows presentation of antigens to T-cells and CD86 interacts with CD28 on T-cells. Concomitant antigen presentation by dendritic cells and B7-co-stimulatory ligand (such as CD80 and CD86) interaction results in T-cell activation. These in vitro data indicate that the microparticles induce changes that are hallmarks of dendritic cell maturation and that are required for induction of innate and adaptive immunity.

Figure 5:
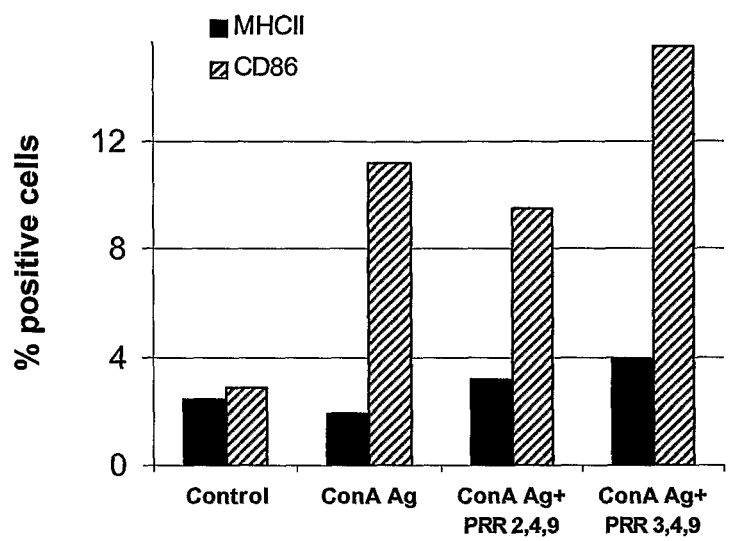
FIG. 5 is a graph showing the induction of MHC-II and CD86 in dendritic cells after exposure to microparticle preparations.

MHC I and MHC II as well as CD80 and CD86 expression on the surface of dendritic cells were determined after 18 hours exposure to different microparticle preparations: control microparticles (control) to which no antigen or PRR agonist was immobilized, and microparticles to which *M. gallisepticum* antigens depleted of ConA binding antigens were immobilized (ConA Ag) with or without the following PRR agonist combinations: 1) PepG, LPS, bacterial DNA (bactDNA) (ConA Ag+PRR 2, 4, 9) or 2) poly I:C, LPS, bactDNA (ConA Ag+PRR 3, 4, 9). The induction of MHC-II and CD86 in dendritic cells is shown in FIG. 5.

The results show the effect of the microparticles on TNF-α secretion by DCs. Control microparticles did not induce a detectable secretion of TNF-α in the conditioned media. The other three types of microparticles (*M. gallisepticum* antigens after depletion of ConA binding antigens and similar antigens co-immobilized with PepG, LPS, bactDNA and poly I:C) induced a significant amount of TNF-α by DCs, compared to control microparticles. Interestingly, the presence of bacterial compounds as immunomodulator generated less TNF-α as compared to the antigens alone. These results indicate that the microparticles do interact with DCs and are able to activate TLRs and NOD receptors to generate a physiological response in accordance with the known effect of these molecules on cells of the immune system. We have demonstrated that microparticles can be targeted to DCs.

Example 24

Purification of Heparin Binding Proteins from MG

*M gallisepticum* was grown as described in Example 2, and the concentrated and washed *mycoplasma* was inactivated as disclosed in step 1 of Example 4. Briefly, to 75 ml crude MG-membrane protein 0.75 Mega-10 was added and the solution mixed for 20 hours at room temperature. Subsequently, 3.75 ml Triton X-100 was added to the solution and mixed for another hour at room temperature. The solution was spun at 5,000 rpm for 10 minutes and supernatant separated from the pellet. Then, 75 ml of Tris buffer (20 mM Tris, 0.1 M NaCl, pH 7.2) was added to the supernatant. Heparin-Actigel column was equilibrated with 5 bed volumes of Tris buffer at 3 ml/min flow rate. The MG-protein solution was loaded onto the column at a flow rate of 8-15 ml/min and the flow through was collected into a separate bottle. The column was washed with 10 bed volumes of Tris buffer at a flow rate of 8-15 ml/min and eluted with a Tris buffer containing 2 M NaCl at a flow rate of 8-15 ml/min. After washing the column with 10 bed volumes of Tris buffer, the MG-protein solution was re-applied to the column and elution repeated as above. The elutions were pooled and dialyzed against Tris buffer using a 3,500 MW cut-off dialysis tubing. Protein assay was performed to determine concentration of eluted proteins.

Example 25

Purification of IgG from Neutralizing Serum and Preparation of Immunoaffinity Column Bulk IgG purification from vaccinated, neutralizing chicken sera and immobilization to Actigel ALD was performed according to Example 3.

Example 26

Tryptic Digestion of Heparin Binding MG Proteins Bound to an Immunoaffinity Column Two mg of purified MG protein was added to a 2 ml immunoaffinity column and allowed to bind for 15 min. The column was washed with 10 ml Tris buffer B (50 mM Tris, pH 7.5, 0.1M NaCl). Trypsin solution, 20 μg/ml in Tris buffer B, was added and the slurry gently agitated for 1 h at 37° C. Fragments and free enzyme were washed away with Tris buffer B and bound peptides eluted with 0.1 M citrate, pH 2.5. The eluate was subsequently neutralized with cc. $NH_4OH$, concentrated and purified on a C-18 reverse phase spin column (Pierce) and analyzed by MALDI-TOF for peptide composition.

Example 27

Tryptic Digestion of Heparin Binding MG Proteins Bound to a Heparin Column

Two mg of purified MG protein was added to 2 ml Heparin Actigel column and allowed to bind for 1 h. The column was washed with 10 ml Tris buffer B. Trypsin solution, 20 μg/ml in Tris buffer B, was added and the slurry gently agitated for 1 h at 37° C. Fragments were washed away with Tris buffer B and bound peptides eluted with Tris buffer B containing 1 M NaCl. The eluate was concentrated and purified on a C-18 reverse phase spin column (Pierce) and analyzed by MALDI-TOF for peptide composition.

Example 28

Purification and Immobilization of C1q Protein

The purification of C1q was carried out following the method of McKay, E J: A simple two-step procedure for the purification of plasma C1q from different animal species. Immunol Letters 1981, 3:303-308. Purified C1q was immobilized to Aminogel (Sterogene Bioseparations, Inc., Carlsbad Calif.) at 3 mg/ml by adaptation of our procedure described in U.S. Pat. No. 5,801,063.

Example 29

Purification and Immobilization of Complement Binding IgG

Polyclonal neutralizing antibodies purified according to Example 24 were applied to a 10 ml column of immobilized C1q, equilibrated in Tris buffer B and allowed to bind for 30 min. Unbound antibodies were removed by washing with 10 bed volumes of Tris buffer B and bound antibodies eluted with the same buffer containing 1 M NaCl. Purified IgG was subsequently immobilized to Actigel ALD at 3 mg/ml.

Example 30

Tryptic Digestion of Complement Activating MG Proteins Bound to an Immunoaffinity Column

*M gallisepticum* was grown as described in Example 2, and the concentrated and washed *mycoplasma* was inactivated as disclosed in step 1 of Example 4. To a 10 ml column of immobilized complement activating antibody, 30 ml of MG lysate was applied at 3 ml/min. The column was washed with 20 bed volumes of Tris buffer B at a flow rate of 8 ml/min to remove non-specifically adsorbed proteins. Trypsin solution, 20 µg/ml in Tris buffer B, was added and the slurry gently agitated for 1 h at 37° C. Fragments were removed by washing with Tris buffer B and bound peptides eluted with 0.1 M citrate, pH 2.5. The eluate was subsequently neutralized with cc. $NH_4OH$, concentrated and purified on a C-18 reverse phase spin column (Pierce) and analyzed by MALDI-TOF for peptide composition.

An example of an immunologically active peptide is shown to have the following composition: Lys-Leu-Ala-Leu-Thr-Ser-Glu-Ile-Thr-Glu-Glu-Ile-Tyr-Pro-Ser-Ala-Pro-Lys-Val-Ser-Arg-Lys-Gln-Arg-Gly-Val-His-Gly-Phe-Ser-Glu-Pro-Thr-Ser (SEQ ID NO: 1). Importantly, this peptide contains the GAG/heparin binding domain of Arg-Lys-Gln-Arg (SEQ ID NO: 6). Another useful sequence is Leu-Leu-Ala-Lys-Lys-Thr-Asp-Lys-Ser-Val-Ser-Pro-Gln-Ala-Ser-Leu-Thr (SEQ ID NO: 2). These sequences can be connected by a linker peptide that contains cleavage sites for endoproteinases. An example of such a linker sequence is LIKFRSN (Leu-Ile-Lys-Phe-Arg-Ser-Asn) (SEQ ID NO: 3). Other linker sequences are known in the art.

Example 31

Synthesis of Antigenic Peptide Epitopes and Multiepitope Peptides

Antigenic peptides were synthesized by the FMOC method.

Example 32

Confirmation of Protective Antigenic Peptides for the Vaccine

Antigenic peptides were mixed with neutralizing sera of vaccinated chickens and the binding inhibition to immobilized heparin is determined by competitive ELISA. A peptide sample is adsorbed to wells of ELISA plates. Subsequently the wells are blocked with blocking solution and immune and non-immune control antisera is subsequently added into the wells and incubated overnight at 4° C. Nonspecific proteins are removed by a wash solution followed by the addition of biotin-labeled heparin at 100 µg/ml diluted in the blocking buffer for 1 h. After washing for 3 times 10 min each of unbound heparin, streptavidin peroxidase is added diluted 1:3,000 in blocking buffer for 1 h. Excess conjugate is removed by washing 3 times 10 min each with wash buffer and color developed by adding 3,3'-diaminobenzidine solution. The signal is inversely proportional to the presence of neutralizing antibodies.

Example 33

Bioinformatics analysis of antigenic proteins of pathogens can also lead to the identification of epitopes of high antigenic potentials. Such an analysis has also been performed for the *M. gallisepticum* MGA protein. The antigenic regions were further analyzed in the context of linear basic motifs. An example of such a predicted highly antigenic linear motif is the sequence: an MHC epitope 10-mer is LLAKKTDKSV (SEQ ID NO: 4) while an MHC-II 16-mer is LLAKKTDKSVSPAQAS (SEQ ID NO: 5). The domains were identified by the SYFPEITHI method. This demonstrates that linear basic motifs are indeed included inside spots of high antigenic propensity. Bioinformatics analysis can be carried out by techniques known in the art such as those described in J. Pevsner, "Bioinformatics and Functional Genomics" (Wiley-Liss, Hoboken, N.J., 2003), using databases and computer analysis for data mining and matching and comparison of sequences known in the art.

Example 34

Purification of Anti-Epitope Antibodies

The identified antigenic peptides are synthesized with a terminal biotin label. The biotin-labeled peptides are immobilized at 1 mg/ml concentration to Avidin Actigel (Sterogene Bioseparations, Inc. Carlsbad, Calif.). Neutralizing antisera from vaccinated chickens were added at saturating concentration and nonspecifically bound proteins were removed by washing with Phosphate buffered saline (PBS), pH 7.2. Specifically bound antibody is eluted with Actisep Elution Medium (Sterogene Bioseparations, Inc. Carlsbad, Calif.).

Advantages of the Invention

The present invention provides improved immune modulatory compositions and methods that can be tailored, for example, to induce an immune response, to elicit a protective immune response, or to elicit tolerance. These compositions are stable and can be prepared with a wide range of immunogens and target molecules in order to bring about the desired effect on the immune response. They provide routes of administration that are in addition to parenteral administration for such agents. They prevent premature breakdown or release of the immunogens and target molecules. The particles have intrinsic mucoadhesive properties which can improve their interaction with mucosal membranes and facilitate uptake. They do not require additional adjuvants.

Methods and compositions according to the present invention utilize the role of N-glycosylation (mannosylation) in immune escape to prevent immune escape from occurring by eliminating appropriate escape epitopes from compositions intended to be used as vaccines. They also utilize the identification of glycosaminoglycan/heparin linear binding motifs and methods to interfere with such binding. Methods and compositions according to the present invention further use a method that has been developed to identify complement activating epitopes. Additionally, methods and compositions according to the present invention utilize the discovery that the use of several TLR agonists greatly enhances the immune response. All antigens and TLR agonists can be targeted to a single cell in the mucosal lymphoid system. Another improved aspect of the invention is the use of synthetic T-cell and B-cell epitopes on a single particle.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

We claim:

1. An immunologically active composition to induce protective immunity, the composition comprising:
   (a) at least one pathogen associated molecular pattern;
   (b) at least one immune active antigen; and
   (c) at least one carrier, wherein the carrier comprises agarose microparticles, and wherein the at least one pathogen associated molecular pattern and the at least one immune active antigen are covalently bound to the agarose microparticles.

2. The composition of claim 1 wherein the at least one immune active antigen does not include an escape epitope.

3. The composition of claim 1, wherein the immune active antigen is a peptide, protein, a recombinant peptide, a recombinant protein, lipid, or carbohydrate.

4. The composition of claim 1, wherein the immune active antigen is a peptide or protein and wherein the peptide or protein possesses immunomodulatory motifs.

5. The composition of claim 1, wherein the immune active antigen is a peptide or protein and wherein the peptide or protein possesses at least one modification involving a carbohydrate moiety, a lipid moiety, or both a carbohydrate and a lipid moiety.

6. The composition of claim 5, wherein the modification contains terminal mannosylation.

7. The composition of claim 5, wherein the modification involves lipid moieties.

8. The composition of claim 1, wherein the immune active antigen is a peptide or protein and wherein the immune active peptide or protein has no modifications involving a carbohydrate moiety, a lipid moiety, or both a carbohydrate and a lipid moiety.

9. The composition of claim 1, wherein the immune active antigen is a peptide or protein and wherein the immune active peptide or protein does not possess amino acid sequences capable of N-glycosylation and/or lipoylation.

10. The composition of claim 1, wherein the immune active antigen is a peptide or protein and wherein the immune active protein or peptide possesses amino acid sequences capable of binding cell surface entry receptors.

11. An immunologically active composition to induce protective immunity, the composition comprising:
    (a) at least one pathogen associated molecular pattern;
    (b) at least one immune active antigen; and
    (c) at least one carrier, wherein the carrier comprises agarose microparticles,
    wherein the at least one pathogen associated molecular pattern and the at least one immune active antigen are covalently bound to the agarose microparticles; and
    wherein the immune active antigen is a peptide or protein and wherein the immune active protein or peptide possesses amino acid sequences capable of binding cell surface glycosaminoglycans (GAGs).

12. An immunologically active composition to induce protective immunity, the composition comprising:
    (a) at least one pathogen associated molecular pattern;
    (b) at least one immune active antigen; and
    (c) at least one carrier, wherein the carrier comprises agarose microparticles,
    wherein the at least one pathogen associated molecular pattern and the at least one immune active antigen are covalently bound to the agarose microparticles; and
    wherein the immune active antigen is a peptide or protein and wherein the immune active protein or peptide possesses amino acid sequences capable of binding cell surface entry receptors; and
    wherein the amino acid sequences are polybasic in nature.

13. The composition of claim 12, wherein the amino acid sequences have the general formula of XBBXBX, XBBBXXBX, BBXXBBBXXBB, BBBXXB, BXBXB, BBB, BXBXXXBXB, or BXBXXXXXBXB wherein B is a basic amino acid and X is any other amino acid.

14. The composition of claim 11, wherein the GAG binding amino acid sequences are capable of generating antibodies to the peptide or protein that are capable of interfering with pathogen binding to cell surfaces.

15. The composition of claim 1, wherein the immune active antigen is capable of generating antibodies to the antigen capable of interfering with pathogen binding to cell entry receptors.

16. The composition of claim 1, wherein the immune active antigen is capable of inducing antibodies capable of interfering with entry into the cell.

17. The composition of claim 1, wherein the immune active antigen is capable of inducing antibodies capable of binding and activating complement.

18. The composition of claim 1, wherein the immune active antigen includes either or both T-cell epitopes and B-cell epitopes.

19. An immunologically active composition to induce protective immunity, the composition comprising:
(a) at least one pathogen associated molecular pattern;
(b) at least one immune active antigen; and
(c) at least one carrier, wherein the carrier comprises agarose microparticles,
wherein the at least one pathogen associated molecular pattern and the at least one immune active antigen are covalently bound to the agarose microparticles; and
wherein the immune active antigen is a peptide or protein and is able to elicit antibodies that can interfere with the binding of N-glycosylation and/or lipoylation sequences to their receptors in the host.

20. An immunologically active composition to induce protective immunity, the composition comprising:
(a) at least one pathogen associated molecular pattern;
(b) at least one immune active antigen; and
(c) at least one carrier, wherein the carrier comprises agarose microparticles,
wherein the at least one pathogen associated molecular pattern and the at least one immune active antigen are covalently bound to the agarose microparticles; and
wherein the immune active antigen is a peptide or protein and is able to elicit antibodies that can interfere with the binding of N-glycosylation and/or lipoylation sequences to the DC-SIGN, L-SIGN or similar receptors in the host.

21. An immunologically active composition to induce protective immunity, the composition comprising:
(a) at least one pathogen associated molecular pattern;
(b) at least one immune active antigen; and
(c) at least one carrier, wherein the carrier comprises agarose microparticles,
wherein the at least one pathogen associated molecular pattern and the at least one immune active antigen are covalently bound to the agarose microparticles; and
wherein the immune active antigen is a peptide or protein and is able to elicit antibodies that can interfere with the binding of N-glycosylation and/or lipoylation sequences to their receptors in the host and prevent or reduce IL-10 production.

22. The composition of claim 1, wherein the pathogen associated molecular pattern is selected from the group consisting of:
(a) a TLR 1 receptor agonist;
(b) a TLR 2 receptor agonist;
(c) a TLR 3 receptor agonist;
(d) a TLR 4 receptor agonist;
(e) a TLR 5 receptor agonist;
(f) a TLR 6 receptor agonist;
(g) a TLR 7 receptor agonist;
(h) a TLR 8 receptor agonist;
(i) a TLR 9 receptor agonist;
(j) a NOD-1 agonist;
(k) a NOD-2 agonist;
(l) an agonist for DC-SIGN;
(m) an agonist for L-SIGN; and
(n) an agonist for a mannose receptor.

23. An immunologically active composition to induce protective immunity, the composition comprising:
(a) at least one pathogen associated molecular pattern;
(b) at least one immune active antigen; and
(c) at least one carrier, wherein the carrier comprises agarose microparticles,
wherein the at least one pathogen associated molecular pattern and the at least one immune active antigen are covalently bound to the agarose microparticles; and
wherein the pathogen associated molecular pattern is a NOD-1 agonist or a NOD-2 agonist and the NOD-1 agonist or NOD-2 agonist is selected from the group consisting of bacterial peptidoglycan and a derivative of bacterial peptidoglycan.

24. The composition of claim 1, wherein the agarose microparticles are porous.

25. The composition of claim 1 comprising more than one immune active antigen covalently attached to the agarose microparticles.

26. The composition of claim 1, wherein more than one immune active antigen and more than one pattern recognition receptor agonist are covalently bound to the agarose microparticles.

27. An immunologically active composition to induce protective immunity, the composition comprising:
(a) at least one pathogen associated molecular pattern;
(b) at least one immune active antigen; and
(c) at least one carrier, wherein the carrier comprises agarose microparticles,
wherein the at least one pathogen associated molecular pattern and the at least one immune active antigen are covalently bound to the agarose microparticles; and
wherein the immune active antigen is a peptide or protein and wherein the peptide or protein possesses immunomodulatory motifs that are hydrophobic in nature and have additional molecules attached to them.

28. The composition of claim 5, wherein the peptide or protein possesses at least one modification involving a carbohydrate moiety, wherein any immunomodulatory terminally mannosylated substances are depleted from the composition by a step selected from the group consisting of an oxidative step, enzymatic treatment, and sugar-specific affinity binding.

* * * * *